(12) United States Patent
Shin et al.

(10) Patent No.: US 11,369,770 B2
(45) Date of Patent: Jun. 28, 2022

(54) BRAIN STIMULATING DEVICE AND USE THEREOF

(71) Applicant: INSTITUTE FOR BASIC SCIENCE, Daejeon (KR)

(72) Inventors: Hee-Sup Shin, Daejeon (KR); Charles Francois Vincent Latchoumane, Daejeon (KR); Jan Born, Tubingen (DE)

(73) Assignee: INSTITUTE FOR BASIC SCIENCE, Daejeon (KR)

( * ) Notice: Subject to any disclaimer, the term of this patent is extended or adjusted under 35 U.S.C. 154(b) by 499 days.

(21) Appl. No.: 16/335,762

(22) PCT Filed: Sep. 22, 2017

(86) PCT No.: PCT/KR2017/010431
§ 371 (c)(1),
(2) Date: Jun. 10, 2019

(87) PCT Pub. No.: WO2018/056733
PCT Pub. Date: Mar. 29, 2018

(65) Prior Publication Data
US 2020/0139113 A1    May 7, 2020

(30) Foreign Application Priority Data

Sep. 23, 2016  (KR) .................. 10-2016-0122501
Jul. 4, 2017    (KR) .................. 10-2017-0085097
(Continued)

(51) Int. Cl.
*A61M 21/00*    (2006.01)
*A61N 1/36*     (2006.01)
(Continued)

(52) U.S. Cl.
CPC ............... *A61M 21/00* (2013.01); *A61N 1/36* (2013.01); *A61N 2/004* (2013.01); *A61N 5/06* (2013.01);
(Continued)

(58) Field of Classification Search
CPC .............. A61N 1/36014; A61N 1/3603; A61N 1/36031; A61N 2007/0026; A61N 2/004;
(Continued)

(56) References Cited

U.S. PATENT DOCUMENTS 8,617,073 B2    12/2013   Prus et al.
2011/0015469 A1  1/2011   Walter et al.
(Continued)

FOREIGN PATENT DOCUMENTS

CN    102783948    11/2012
CN    104706423    6/2015
(Continued)

OTHER PUBLICATIONS

Dorothée Coppieters 'tWallant et al., "Sleep Spindles as an Electrographic Element: Description and Automatic Detection Methods", Neural Plasticity, vol. 2016, Jul. 11, 2016 (Jul. 11, 2016), pp. 1-19.
(Continued)

*Primary Examiner* — Carrie R Dorna
(74) *Attorney, Agent, or Firm* — Lex IP Meister, PLLC

(57) ABSTRACT

The present invention relates to a brain stimulating device and, particularly, relates to a brain stimulating device comprising: a brainwave measurement unit for outputting a brainwave signal; and a stimulation unit for applying spindle-like stimulation to a brain in accordance with the generation of slow oscillation included in the brainwave signal. The brain stimulating device according to the present invention can reinforce memory or reduce memory deterio-
(Continued)

ration due to dementia. Also, the brain stimulating device according to the present invention can reinforce hippocampus-dependent memory. Further, a portable device according to the present invention can control and monitor the brain stimulating device. Moreover, a method for assessing the performance of the brain stimulating device according to the present invention can assess the performance of the brain stimulating device.

3 Claims, 21 Drawing Sheets

(30) Foreign Application Priority Data

Sep. 21, 2017 (KR) .................. 10-2017-0121854
Sep. 21, 2017 (KR) .................. 10-2017-0121855

(51) Int. Cl.
*A61N 5/06* (2006.01)
*A61N 7/00* (2006.01)
*A61N 2/00* (2006.01)

(52) U.S. Cl.
CPC ........ *A61N 7/00* (2013.01); *A61N 2007/0026* (2013.01)

(58) Field of Classification Search
CPC ......... A61N 2/006; A61N 2/02; A61M 21/00; A61M 21/02; A61M 2021/0005; A61M 2021/0022; A61M 2021/0027; A61M 2021/0044; A61M 2021/0055; A61M 2021/0072
See application file for complete search history.

(56) References Cited

U.S. PATENT DOCUMENTS

| | | | |
|---|---|---|---|
| 2011/0112394 A1 | 5/2011 | Mishelevich | |
| 2012/0296390 A1 | 11/2012 | Nakashima et al. | |
| 2014/0057232 A1* | 2/2014 | Wetmore | A61N 1/36025 434/236 |
| 2014/0316217 A1 | 10/2014 | Purdon et al. | |
| 2015/0148710 A1 | 5/2015 | Towe et al. | |
| 2015/0164361 A1 | 6/2015 | Lunner | |
| 2015/0297109 A1* | 10/2015 | Garten | A61B 5/375 600/544 |
| 2016/0220783 A1 | 8/2016 | Garcia Molina | |
| 2016/0242648 A1 | 8/2016 | Konofagou et al. | |
| 2017/0340854 A1* | 11/2017 | Geerlings | A61B 5/4836 |

FOREIGN PATENT DOCUMENTS

| | | | |
|---|---|---|---|
| EP | 2524649 | 11/2012 | |
| EP | 2883494 | 6/2015 | |
| JP | S62-155863 | 7/1987 | |
| JP | 2010-504843 | 2/2010 | |
| JP | 2012-239696 | 12/2012 | |
| KR | 10-0743967 | 7/2007 | |
| KR | 10-1114299 | 2/2012 | |
| KR | 10-1140507 | 4/2012 | |
| KR | 10-1465613 | 11/2014 | |
| WO | 2008-039930 | 4/2008 | |
| WO | 2009/126179 | 10/2009 | |
| WO | 2016-005870 | 1/2016 | |
| WO | WO-2016028635 A1 * | 2/2016 | ............. A61B 5/375 |
| WO | 2016/102602 | 6/2016 | |
| WO | 2018-056733 | 3/2018 | |

OTHER PUBLICATIONS

JPO, Office Action of JP 2019-516141 dated Jun. 9, 2020.
EPO, Supplementary European Search Report of EP 17853447.5 dated Jul. 8, 2020.
SIPO, Office Action of application No. 201780071497.8 dated Jan. 8, 2021.
Gabrielle Girardeau et al., "Selective suppression of hippocampal ripples impairs spatial memory", Nature Neuroscience, vol. 12, No. 10, Oct. 2009.
Til O. Bergmann et al., "Sleep spindle-related reactivation of category-specific cortical regions after learning face-scene associations", NeuroImage, vol. 59, pp. 2733-2742, 2012.
Angela Kima et al., "Optogenetically induced sleep spindle rhythms alter sleep architectures in mice", PNAS, vol. 109, No. 50, Dec. 2012.
Erin J. Wamsley, PhD et al., "Reduced sleep spindles and spindle coherence in schizophrenia: Mechanisms of impaired memory consolidation?", Biol Psychiatry, vol. 71, No. 2, pp. 154-161, Jan. 2012.
Sonja Binder et al., "Transcranial Slow Oscillation Stimulation During Sleep Enhances Memory Consolidation in Rats", Brain Stimulation, vol. 7, pp. 508-515, 2014.
Robert Göder et al., "Impairment of sleep-related memory consolidation in schizophrenia: relevance of sleep spindles?", Sleep Medicine, vol. 16, pp. 564-569, 2015.
Matthias Mölle, PhD et al., "Fast and Slow Spindles during the Sleep Slow Oscillation: Disparate Coalescence and Engagement in Memory Processing", SLEEP, vol. 34, No. 10, 2011.
Hong-Viet V. Ngo et al., "Auditory Closed-Loop Stimulation of the Sleep Slow Oscillation Enhances Memory", Neuron, vol. 78, pp. 545-553, May 2013.
KIPO, Office Action of KR 10-2017-0121854 dated Aug. 17, 2018.
KIPO, Office Action of KR 10-2017-0121855 dated Aug. 21, 2018.

* cited by examiner

BRAIN STIMULATING DEVICE AND USE THEREOF

TECHNICAL FIELD

The present invention relates to a brain-stimulating device and the use thereof, and more particularly to a brain-stimulating device comprising an EEG measurement unit that measures an EEG signal, and a stimulation unit that applies a spindle-like stimulation to a brain in response to the generation of a slow oscillation included in the EEG signal, and a method of enhancing memory using the same.

BACKGROUND ART

The characteristics of an electroencephalogram (EEG, also called 'brainwave') and an electrocardiogram (ECG) which will be described are used as an objective indicator for assessment of brain activity. In general, "EEG" refers to a scalp EEG recorded from a scalp electrode. The electroencephalogram (EEG) is a medical test that can simply assess a cerebral function in an objective, noninvasive and continuous manner. It can be seen from the EEG that the function of the brain, particularly the activity of the brain is decreased or increased. In other words, the EEG is an objective indicator that represents the level of the activity of the brain. Thus, the value of the electroencephalogram (EEG) test is recognized spatiotemporally as being capable of identifying momentary changes in the brain activity. Korean Patent No. 10-145613 (registered on Jan. 20, 2014) discloses a head-wearing device that is worn on a head (i.e., nerocranium) so that an electric stimulus can be applied to a specific area of the brain and simultaneously an EEG can be measured.

Electrical activity of the brain reflected on the EEG is determined by neurons, gila cells, and the blood-brain barrier, and it is mainly caused by the neurons. The gila cells that account for half of the brain's weight regulate the flow of ions and molecules in a synapse which is a region between two adjacent neurons, and function to maintain, support, and repair the structures between neurons. The blood-brain barrier serves to selectively pass only necessary ones among from various substances in the brain's blood vessels. The changes in the EEG by the gila cells and the blood-brain barrier occur slowly whereas the changes in the EEG by the activity of the neurons occur considerably and rapidly in various manners.

In general, the brainwave is divided into a delta wave (0.2-3.99 Hz), a theta wave (4-7.99 Hz), an alpha wave (8-12.99 Hz), a beta wave (13-29.99 Hz), and a gamma wave (30-50 Hz) according to the range of the oscillation frequency. It has been demonstrated that the theta wave has a low-frequency range and is an area that displays memory, creativity and learning ability, and manifests a human's potential (U.S. Patent Publication No. 2016-0220783, U.S. Patent Publication No. 2011-0015469, and PCT International Patent Publication No. WO2016/005870).

Thus, an optimal level of arousal state that can maximally display information throughput, memory, concentration, etc., of the brain is a state in which the brainwaves having a relatively low frequency such as the alpha wave and the theta wave are emitted. Various potential programs including unconscious reactions and psychological causes, personality, habit stickiness, etc., of the human are recorded in the theta wave region. The development of the theta wave region is correlated with manifestation of the remaining 70% potential beyond the alpha and beta wave regions of less than 30%, which are utilized by the human.

A neural network oscillation of different frequencies is defined as a basic mechanism of a wide range of network information exchange of a brain awakened by the interaction between the oscillation rhythms. The combination of crossover frequencies between gamma, beta and theta rhythms activates the neural firing activity so as to control attention, encoding and information integration between brain areas that are remote from each other. However, it is unclear whether or not an information process of a brain in a sleep state follows the principle of a brain in an awakened state.

Sleep is known to support the consolidation of memory. The 1>Hz cortical slow oscillation, thalamo-cortical spindles (7-15 Hz), and hippocampal sharp-wave ripples (100-250 Hz) represent the cardinal rhythms of a slow wave sleep state, and all these rhythms have been implicated in the consolidation of hippocampus-dependent memory during sleep. Phase-locking is caused by oscillation of the up-state spindle with ripples accompanied by a reactivation of the neural memory in the hippocampus. The phase-locking is presumed to be related to the hippocampus close to the neocortical network, which is a long-term storage site. So far, there is no experimental evidence that these phase-locking rhythms form memory in connection with the spindles, and it is presumed that the spindle emerging in the course of human nocturnal sleep plays an important role in forming memories during sleep. (Gabrielle Girardeau et al., 2009, Nature Neuroscience; Til O. Bergmann et al., 2011, NeuroImage; Kim et al., 2012, PNAS; Erin J. Wamsley et la., 2012, BIOL PSYCHIATRY.; Sonja Binder et al., 2014, Brain Stimulation; Robert Goder et al., 2015, Sleep Medicine).

Under this technical background, the inventors of this application have made extensive efforts to develop a method of enhancing memory through effective brain stimulation, and as a result, have found that when an artificial spindle-like signal is applied to the brain, a substantial spindle is induced to the brain to reinforce a memory (e.g., hippocampus-dependent memory), thereby completing the present invention.

The information disclosed in the Background Art section is only for the enhancement of understanding of the background of the present invention, and therefore may not contain information that forms a prior art that would already be known to a person of ordinary skill in the art.

DISCLOSURE OF INVENTION

Technical Problem

It is an object of the present invention to provide a brain-stimulating device that can reinforce a memory or reduce degradation of the memory due to dementia.

Another object of the present invention is to provide a portable device that can control and monitor the brain-stimulating device.

Still another object of the present invention is to provide a method that can assess the performance of the brain-stimulating device.

Yet another object of the present invention is to provide a method that can increase memory using the brain-stimulating device.

Technical Solution

To achieve the above object, the present invention provides a brain-stimulating device comprising: an EEG measurement unit configured to measure an EEG signal, and a stimulation unit configured to apply spindle-like stimulation to a brain in response to the generation of a slow oscillation included in the EEG signal.

The present invention also provides a portable device configured to be operated in cooperation with the brain-stimulating device, the portable device comprising: a communication unit configured to perform communication with the brain-stimulating device; and a touch display unit, wherein the touch display unit displays any one of selected from the group consisting of: an image necessary for controlling the intensity of spindle-like stimulation; an image necessary for controlling the phase difference between a slow oscillation component of the spindle-like stimulation and slow oscillation included in an EEG signal; and an image necessary for controlling the on/off operation of the brain-stimulating device.

The present invention also provides a portable device configured to be operated in cooperation with the brain-stimulating device, the portable device comprising: a communication unit configured to perform communication with the brain-stimulating device; and a display unit, wherein the touch display unit displays any one of selected from the group consisting of: a degree in which a spindle-like stimulation is applied; a degree in which a spindle is induced to a brain by the spindle-like stimulation; and a degree in which the brain-stimulating device is operated.

The present invention also provides a method for assessing the performance of a brain-stimulating device, the method comprising: (a) providing an object to be memorized of a user to the touch display unit of the portable device of the present invention before sleep; (b) turning on or off the brain-stimulating device during sleep; and (c) performing a step of providing a screen for testing a degree of memorization of the to-be-memorized object of the user after sleep, several times, then displaying a difference in the degree of memorization according to the on or off operation of the brain-stimulating device.

The present invention also provides a method for enhancing memory, the method comprising: (a) providing an object to be memorized to a user before sleep; and (b) stimulating a brain using the brain-stimulating device during sleep.

BRIEF DESCRIPTION OF THE DRAWINGS

FIG. 4 is a view showing an example of signals included in FIG. 3, wherein FIG. 4(a) shows an example of a state after passing of a signal measured in an EEG measurement unit through a filter, FIG. 4(b) shows a slow oscillation detection signal in an EEG signal of FIG. 4(a), FIG. 4(c) shows an up-state signal corresponding to the up-state of the slow oscillation, FIG. 4(d) shows a stimulation control signal generated from a stimulation control signal generation unit during the output of the up-state signal, and FIG. 4(e) shows spindle-like stimulation applied to a brain in response to the stimulation control signal.

FIG. 18 is a graph showing a ratio of spindles generated within a time interval of 750 ms after optogenetic stimulation starts, wherein FIG. 18(a) shows the prefrontal lobe (FRO) EEG, measured within a time interval of 750 ms after spindle-like stimulation is applied, and FIG. 18(b) shows the hippocampal (CA1) EEG, measured within a time interval of 750 ms after spindle-like stimulation is applied.

FIG. 24(B) is an image obtained by photographing the scene of actually performing an ultrasonic stimulation experiment on a mouse brain, FIG. 24(C) schematically shows a stimulation method in which stimulation is applied with 50,000 repetitions at 150 kHz, and FIG. 24(D) is an EEG graph showing measurement of EEGs generated during the application of stimulation.

BEST MODE FOR CARRYING OUT THE INVENTION

Figure 1:
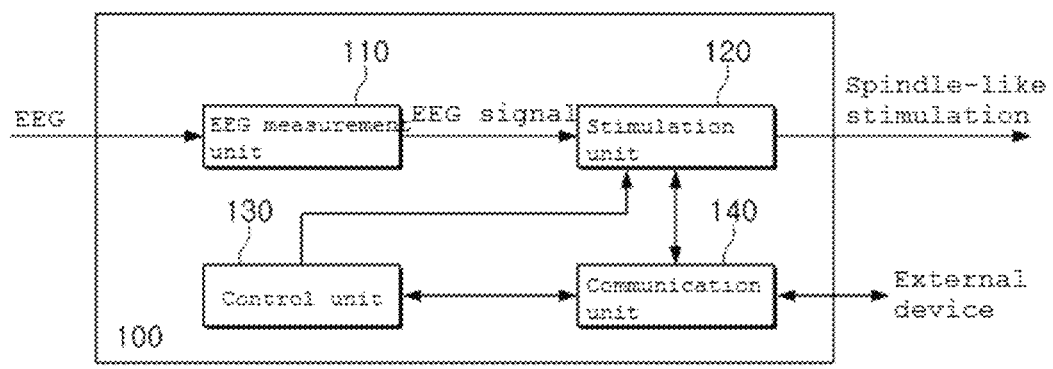
FIG. 1 shows a block diagram showing a configuration of a brain-stimulating device according to an embodiment of the present invention.

While the invention can be modified in various ways and take on various alternative forms, specific embodiments thereof are shown in the drawings and will be described in detail below as examples. It should be understood, however, that there is no intent to limit the invention to the particular forms disclosed, but on the contrary, the invention is to cover all modifications, equivalents, and alternatives falling within the spirit and scope of the appended claims.

It will be understood that, although the terms "first", "second", "A", "B", etc. may be used herein to describe various elements of the invention, these elements should not be limited by these terms. The terms are used only to distinguish an element from another. For example, a first element could be termed a second element, and, similarly, a second element could be termed a first element, without departing from the scope of the present invention. As used herein, the term "and/or" includes any and all combinations of one or more of the associated listed items.

As used herein, the singular forms "a," "an" and "the" are intended to include the plural forms as well, unless the context clearly indicates otherwise. It will be further understood that the terms "comprises," "comprising," "includes," and/or "including," when used herein, specify the presence of stated features, numbers, steps, operations, elements, components, and/or combinations thereof but do not preclude the presence or addition of one or more other features, numbers, steps, operations, elements, components, and/or combinations thereof.

Before starting detailed explanations of figures, components that will be described in the specification are discriminated merely according to functions mainly performed by the components or conventionally carried out according to common knowledge of related technical fields. That is, two or more components which will be described later can be integrated into a single component. Furthermore, a single component which will be described later can be separated into two or more components. Moreover, it is, of course, to be noted that each component which will be described can additionally perform some or all of a function executed by another component in addition to the main function thereof. Some or all of the main function of each component which will be described can be carried out by another component.

Also, in the execution of a method or an operation method, unless the context clearly indicates a specific order, steps constituting the method may be executed differently from the specified order. That is, the steps may be executed in the same order as specified, may be executed substantially concurrently, or may be executed in a reverse order.

As used herein, the term "spindle" refers to a spindle-shaped EEG appearing during measurement of an EEG, and the spindle may appear within a frequency range from about 11 Hz to about 16 Hz during the measurement of the EEG, but is not limited thereto.

As used herein, the term "slow oscillation" refers to an EEG generated during slow wave sleep. The slow oscillation may be mainly generated in neocortical networks, and may have a frequency of about 1 Hz or less, but is not limited thereto.

As used herein, the term "spindle-like stimulation" is comprised of a spindle component and a slow oscillation component, and is a signal generated to induce a spindle-shaped EEG from a brain. The spindle component of the spindle-like stimulation may have a spindle-like frequency of the human EEG, and the slow oscillation component may have a slow oscillation-like frequency of the human EEG.

As used herein, the term "ripple" refers to an EEG appearing in hippocampus during measurement of the EEG. For humans, the ripple may be measured to have a frequency range from 140 to 220 Hz, but is not limited thereto.

As used herein, the term "in-phase" refers to phase difference of 0 degree between both EEGs, i.e., the condition where both EEGs have the same as each other in terms of wavelength, amplitude, frequency and waveform to exhibit the same shape.

In the present invention, it was confirmed that spindle-like stimulation repeated during sleep exhibits the same effect as in the memory processing by the cortical slow oscillation, the cortico-thalamic spindle, and hippocampal ripple oscillation in the slow wave sleep state.

In particular, thalamic spindles were found to induce up-state cortical slow oscillation, and promote consolidation of hippocampus-dependent memory during sleep. In addition, the thalamic spindles were found to perform an important function of connecting rhythms of the hippocampal ripples and the cortical slow oscillation between spindles. By virtue of this, it was confirmed that while stimulation is rippled to long-term storage sites of neocortical regions, the spindles support efficient consolidation of memory information between hippocampi.

In one example of the present invention, it was found that when spindle-like stimulation (four light-pulses, 62.5 ms on/off duration) is applied to mice in the slow wave sleep state, it exhibits the same effect as in the spindle stimulation. In addition, it was also found that when slow oscillation (500 ms duration) is continuously applied to mice in the state of being susceptible to TRN inhibition, fear memory disappear remarkably. Further, it was found that mice receiving stimulation with the slow oscillation during slow wave sleep after learning showed enhanced place memory.

Thus, in one aspect, the present invention is directed to a brain-stimulating device comprising: (a) an EEG measurement unit configured to measure an EEG signal of a brain; and (b) a stimulation unit configured to apply a spindle-like stimulation to the brain in response to the generation of a slow oscillation included in the EEG signal.

Figure 2:
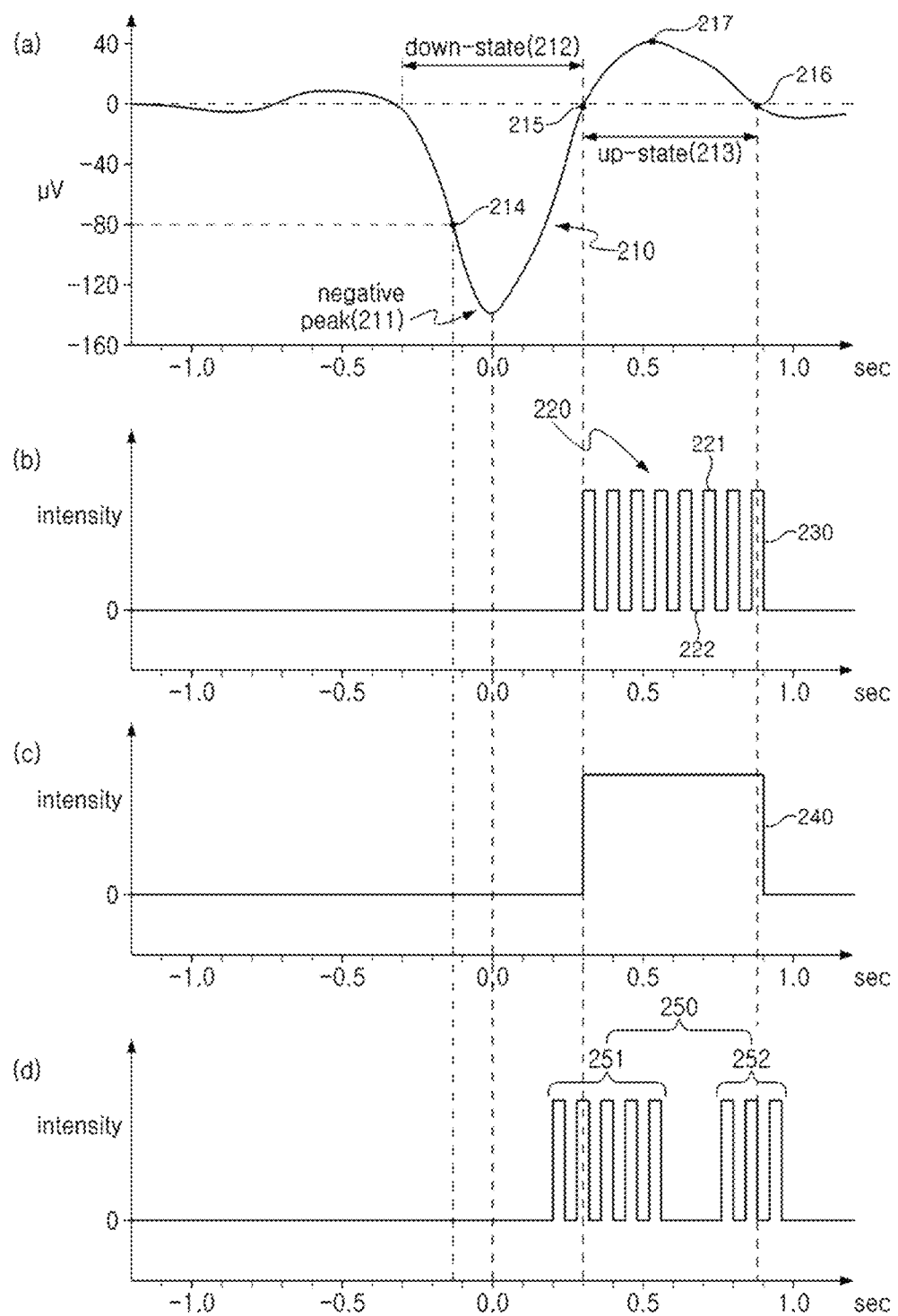
FIG. 2 is a view showing the relationship between slow oscillation and spindle-like stimulation, wherein FIG. 2(a) schematically shows an example of slow oscillation, FIG. 2(b) schematically shows an example of a spindle component of the spindle-like stimulation, FIG. 2(c) schematically shows an example of a slow oscillation component of the spindle-like stimulation, and FIG. 2(d) schematically shows an example of application of the spindle component of the spindle-like stimulation at regular intervals.

FIG. 1 shows a block diagram showing a configuration of a brain-stimulating device according to an embodiment of the present invention. FIG. 2 is a view showing the relationship between slow oscillation and spindle-like stimulation. Hereinafter, the brain-stimulating device according to the present invention will be described with reference to FIGS. 1 and 2.

Referring to FIG. 1, the brain-stimulating device 100 includes an EEG measurement unit 110 and a stimulation unit 120. The brain-stimulating device 100 may further include a control unit 130 and a communication unit 140.

The EEG measurement unit 110 outputs an EEG signal corresponding to an EEG of the brain. For example, the EEG measurement unit 110 measures a scalp EEG. The EEG measurement unit 110 measures, for example, a prefrontal lobe EEG. To this end, the EEG measurement unit 110 includes at least one measurement electrode (not shown) arranged on a prefrontal scalp. The measurement electrode may be disposed on any one of left, central and right of the prefrontal scalp. Additional measurement electrodes may be disposed on a frontal lobe scalp or parietal lobe scalp. The EEG measurement unit 110 further includes a reference electrode (not shown). The reference electrode may be disposed on an at least one selected from the group consisting of an occipital lobe scalp, a left ear and a right ear.

The stimulation unit 120 applies spindle-like stimulation to the brain in response to the generation of a slow oscillation included in the EEG signal. The slow oscillation, which is an EEG mainly generated during slow wave sleep, is known to have a frequency of 1 Hz or less. The slow oscillation is known to be mainly generated in neocortical networks. The slow oscillation is disclosed in a large amount of literature, including a paper "Fast and Slow Spindles during the Sleep Slow Oscillation: Disparate Coalescence and Engagement in Memory Processing, Matthias Mölle et al., 2011, SLEEP" and "Auditory Closed-Loop Stimulation of the Sleep Slow Oscillation Enhances Memory, Hong-Viet V. Ngo et al., 2013, Neuron Article, Cell press". An example of the slow oscillation is shown in FIG. 2(a). In FIG. 2(a), a slow oscillation 210 is shown using a negative peak 211 as a reference. A period in which the slow oscillation 210 includes the negative peak 211 and has a negative voltage is referred to as a downstate 212. A period in which the slow oscillation 210 has a positive voltage is referred to as an upstate 213, which is subsequent to the downstate 212.

The generation of the slow oscillation can be determined by various methods. For example, if an EEG signal having passed through a filter (not shown) is smaller than or equals to a threshold value, it can be determined that the slow oscillation is generated. The threshold value may be a fixed or variable value. As the variable threshold value, a value inputted by a user or a manufacturer, or a value changing depending on an EEG signal may be used. As a value changing depending on an EEG signal, a value obtained by multiplying an average or a standard deviation of the EEG signal having passed through the filer by a constant may be used. In FIG. 2(a), there is shown an example in which the generation of the slow oscillation is determined depending on a fixed threshold value (e.g., 80 μV).

A spindle-like stimulation is applied to a brain in response to the generation of the slow oscillation. For example, the spindle-like stimulation is outputted after the generation of the slow oscillation. The spindle-like stimulation 220 may start immediately after the generation of the slow oscillation, but may start at a time interval from the generation 214 of the slow oscillation, as shown in FIGS. 2(a) and 2(b). As a first example, the spindle-like stimulation 220 may start after the lapse of a first period, following the generation 214 of the slow oscillation. As a second example, the spindle-like stimulation 220 may start after the lapse of a second period after the generation of the slow oscillation, followed by the generation of the negative peak 211. As a third example, the spindle-like stimulation 220 may start after the generation of the slow oscillation, immediately followed by the occurrence of an event 215 where the voltage of the slow oscillation is changed from negative one to positive one. As a fourth example, the spindle-like stimulation 220 may start after the generation of the slow oscillation, immediately followed by the generation of a positive peak 217. The first and second periods may be fixed or variable values. As the variable values, values inputted by a user or a manufacturer, or the like may be used.

The duration of the spindle-like stimulation 220 may be determined in various manners. As a first example, as shown in FIG. 2(b), the spindle-like stimulation 220 may end after the lapse of a first period (e.g., 0.6 sec), following the start of the spindle-like stimulation. As a second example, the spindle-like stimulation 220 may continue until the occurrence of an event 216 where the voltage of the slow oscillation 210 is changed from positive one to negative one. As a third example, as shown in FIG. 2(d), the spindle-like stimulation 250 may continue during a second period 251 after the start thereof, stop during a third period, and again continue during a fourth period 252. The first to fourth periods may be fixed or variable values. As the variable values, values inputted by a user or a manufacturer, or the like may be used.

In the present invention, the spindle-like stimulation 220 may include a spindle component 230 having a spindle-like frequency of the EEG and a slow oscillation component 240 having a slow oscillation-like frequency of the EEG. The slow oscillation component 240 is a concept similar to that of an envelope of the spindle-like stimulation 220, and may be a signal from which a high frequency component has been removed.

In the present invention, the slow oscillation component 240 of the spindle-like stimulation 220 may be substantially in-phase with the slow oscillation of the EEG.

As used herein, "substantially in-phase" is a concept broader than a concept in which the phases of the slow oscillation component 240 and the slow oscillation 210 completely coincide with each other. In other words, the phases of the slow oscillation component 240 and the slow oscillation 210 may do not coincide with each other due to an issue of implementation or other reasons (e.g., sacrifice of the effect of the present invention for the purpose of further improvement), the substantially in-phase is a broad concept including even this case. After the detection of the generation of the slow oscillation 210, the generation of the spindle-like stimulation 220 starts immediately after the occurrence of the event 215 where the voltage of the slow oscillation 210 is changed from negative one to positive one. In this case, even though the generation of the spindle-like stimulation 220 stops immediately after the occurrence of the event 216 where the voltage of the slow oscillation 210 is changed from positive one to negative one, the phases of the slow oscillation component 240 and the slow oscillation 210 do not slightly coincide with each other due to a delay of various circuits included in the brain-stimulating device and a filter for extracting the slow oscillation 210. As a first example considering simplicity of implementation, the generation of the spindle-like stimulation 220 may start after the lapse of a first period (e.g., 0.4 sec), following the generation 214 of the slow oscillation. Then, the generation of the spindle-like stimulation 220 may stop after the lapse of a second period (e.g., 0.5 sec), following the start of the generation of the spindle-like stimulation 220. As a second example considering simplicity of implementation, the generation of the spindle-like stimulation 220 may start after the lapse of a third period (e.g., 0.3 sec), following the generation 211 of the negative peak, and then the generation of the spindle-like stimulation 220 may stop after the lapse of a fourth period (e.g., 0.5 sec), following the start of the generation of the spindle-like stimulation 220. The first to fourth periods may be values obtained through the measurement experiment on several subjects. In addition, the first to fourth periods may be fixed values in terms of a hardware configuration or variable values in terms of a software configuration. As an example in which the slow oscillation component 240 is substantially in-phase with the slow oscillation 210, the generation of the spindle-like stimulation 220 may start during a period between 0.2 sec before and 0.2 sec after the occurrence of the event 215 where the voltage of the slow oscillation 210 is changed from negative one to positive one. In addition, the generation of the spindle-like stimulation 220 may stop during a period between 0.2 sec before and 0.2 sec after the occurrence of the event 216 where the voltage of the slow oscillation 210 is changed from positive one to negative one.

In the present invention, the spindle-like stimulation may be modified in various manners. For example, as shown in FIG. 2(d), the spindle-like stimulation 250 may be divided into two regions 251 and 252 that are spaced apart from each other. Even in this case, the amount of the spindle-like stimulation 250 applied to the brain during the up-state period 213 of the slow oscillation 210 is larger than that of the spindle-like stimulation 250 applied to the brain during the period other than the up-state period. For example, the intensity of the spindle-like stimulation 250 applied to the brain during the up-state period 213 of the slow oscillation 210 may be more than two times higher than that of the spindle-like stimulation 250 applied to the brain during the period other than the up-state period.

In the present invention, the frequency of the spindle component 230 of the spindle-like stimulation 220 may be within the spindle frequency range generated from the brain. In the present invention, the spindle frequency generated from the brain may be within a frequency range from 11 to 16 Hz. In the present invention, the frequency of the spindle component 230 necessarily needs not to be within the above frequency range. The frequency of the spindle component 230 may be a fixed value in terms of a hardware configuration, and may be a variable value in terms of a software configuration. In addition, the frequency of the spindle component 230 may be variable depending on the frequency of the spindle measured from the brain. Thus, the frequency of the spindle component 230 may be a fixed or variable value. As the variable frequency, a value inputted by a user or a manufacturer, or a value changing depending on a spindle frequency measured from an EEG signal may be used.

In the present invention, the phase of the spindle component 230 may be substantially in-phase with the spindle of the EEG signal.

As used herein, "substantially in-phase" is a concept broader than a concept in which the phases of the spindle component 230 and the spindle completely coincide with each other. In other words, the phases of the spindle component 230 and the spindle may do not coincide with each other due to an issue of implementation or other reasons, and the substantially in-phase is a broad concept including even this case.

In the present invention, the spindle-like stimulation 220 may be applied to the brain during the non-rapid eye movement (NREM) sleep period. For example, the spindle-like stimulation 220 may be applied to the brain in a slow wave sleep state during the NREM sleep period.

In the present invention, the spindle-like stimulation may use various type stimulations. Preferably, the stimulation may include at least one selected from the group consisting of vibratory stimulation, electric stimulation, magnetic stimulation, electromagnetic wave stimulation, sonic wave stimulation, ultrasonic wave stimulation, and optogenetic stimulation. In FIG. 2(b), when the spindle-like stimulation 220 has a higher level (221), an ultrasonic wave is applied to the brain as an example of the stimulation whereas when the spindle-like stimulation 220 has a lower level (222), no stimulation or a very low stimulation is applied to the brain. In other words, the amplitude of the ultrasonic wave is controlled to be "0". The stimulation unit 120 may directly or indirectly apply the stimulation to the brain. As an example of the indirectly applied stimulation, the stimulation is applied to a visual, auditory, tactile, gustatory or olfactory nerve so as to be delivered to the brain. For example, the brain may be stimulated using sound of a specific frequency, may be stimulated through eye stimulation using an optical pulse of a specific frequency, and may be stimulated through olfactory or gustatory stimulation using a specific compound.

The stimulation unit 120 may apply the stimulation, as one example, to an unspecific region of the brain, i.e., the entire brain. As another example, the stimulation unit 120 may apply the spindle-like stimulation to a partial region of the brain. The partial brain region may be a thalamic reticular nucleus.

In the present invention, the spindle-like stimulation may be selected from the group consisting of vibratory stimulation, electric stimulation, magnetic stimulation, electromagnetic wave stimulation, sonic wave stimulation, ultrasonic wave stimulation, and optogenetic stimulation. A focused ultrasound device may be used to apply the stimulation to the partial region of the brain. The focused ultrasound device is configured to allow ultrasound to be focused onto the partial brain region to which the stimulation is to be applied. The focused ultrasound device used as the stimulation unit 120 delivers a relatively low energy compared to high-intensity focused ultrasound (HIFU) used as substitute of surgery. Examples of the focused ultrasound device are disclosed in U.S. Patent Publication No. 2016-0242648 (entitled "SYSTEMS AND METHODS FOR NON-INVASIVE BRAIN STIMULATION WITH ULTRASOUND"), U.S. Patent Publication No. 2015-0148710 (entitled "Ultrasound Modulation of the Brain for Treatment of Stroke, Brain Injury, and Other Neurological Disorders"), U.S. Pat. No. 8,617,073 (entitled "Focusing ultrasound into the brain through the skull by utilizing both longitudinal and shear waves"), and U.S. Patent Publication No. 2011-0112394 (entitled "NEUROMODULATION OF DEEP-BRAIN TARGETS USING FOCUSED ULTRASOUND").

In the present invention, in the case where an oscillation device is used as the stimulation unit 120, the oscillation device may be an oscillation generating device comprising: a power source unit configured to supply electric power to a circuit and a micro oscillation motor; an oscillation intensity setting unit configured to set the oscillation intensity of the oscillation motor; a driving unit configured to receive an oscillation intensity set value from the oscillation intensity setting unit to control the rotation of the oscillation motor; an amplification unit configured to amplify an output signal from a microcomputer to a signal level that can drive the micro motor to drive the micro motor; and an oscillation generating motor unit configured to be attached closely to a brain to provide oscillation to the brain.

In the present invention, in the case where an electric stimulation method is used as the stimulation unit 120, the electric stimulation method may include a deep electrical stimulation method, a transcranial magnetic stimulation (TMS) method, and a transcranial electrical stimulation (TES) method, particularly a transcranial direct current stimulation (tDCS) method and a transcranial random noise stimulation (tRNS) method.

In the present invention, in the case where an electromagnetic wave stimulation device is used as the stimulation unit 120, the electromagnetic wave stimulation device may include one or more coils configured to generate electric current, and a magnetic field generating device configured to allow the electric current to pass through skin and the like so as to stimulate the brain. The electromagnetic wave stimulation device may include a device that is configured to intravenously inject nanoparticles containing various ion types of iron ions, and then apply a low-energy magnetic field to allow the nanoparticles to induce local electric charge oscillation to stimulate the brain.

In the present invention, in the case where an optogenetic stimulation device is used as the stimulation unit 120, the optogenetic stimulation device may include a device configured to invasively deliver optical stimulation to a specific region of the brain through an optical fiber cannula (OPT).

The control unit 130 controls the operation of the stimulation unit 120. For example, the control unit 130 controls the intensity of the spindle-like stimulation 220. Herein, "intensity of the spindle-like stimulation" refers to a magnitude of the spindle-like stimulation that can apply stimulation to the brain, such as frequency, pulse width, oscillation period or the like. As a first example, the intensity of the spindle-like stimulation 220 may be controlled depending on the setting of a user. As a second example, the intensity of the spindle-like stimulation 220 may be controlled depending on a time period. The control unit 130 may control the intensity of the spindle-like stimulation to be weakened during an initial slow wave sleep period of the entire sleep period, and control the intensity of the spindle-like stimulation to be strengthened during a slow wave sleep period following an intermediate sleep period. The control unit 130 may control the intensity of the spindle-like stimulation to be weakened during a first period (e.g., 01:00 am to 02:00 am), control the intensity of the spindle-like stimulation to be strengthened during a second period (e.g., 02:00 am to 06:00 am), and control the intensity of the spindle-like stimulation to be weakened during a third period (e.g., 06:00 am to 08:00 am). As a third example, the intensity of the spindle-like stimulation 220 may be controlled depending on the intensity of a spindle induced by the spindle-like stimulation. The control unit 130 may control the intensity of the spindle-like stimulation to be weakened if the intensity of the induced spindle is higher than a first reference value, and control the intensity of the spindle-like stimulation to be strengthened if the intensity of the induced spindle is lower than a second reference value which is lower the first reference value.

The control unit 130 controls a phase difference between the slow oscillation component 240 of the spindle-like stimulation 220 and the slow oscillation 210 included in the EEG signal. For example, the control unit 130 may control the start time point of the slow oscillation component 240 to be more delayed by 0.2 sec or preceded by 0.1 sec than the start time point of the up-state of the slow oscillation 210. Also, the control unit 130 may control the end time point of the slow oscillation component 240 to be more delayed by 0.3 sec or preceded by 0.2 sec than the end time point of the up-state of the slow oscillation 210.

The control unit 130 controls the on/off operation of the stimulation unit 120. For example, the control unit 130 controls the supply of power to the stimulation unit 120 to control the on/off operation of the stimulation unit 120. For example, the control unit 130 may control the on/off operation of the stimulation unit 120 depending on a timer value set by a user or a software program. As a first example using a timer, if the timer value is set to 1 hour, the control unit 130 may control the stimulation unit 120 to be maintained in an off state before the lapse of 1 hour, and then control the stimulation unit 120 to be maintained in an on state after the lapse of 1 hour. In addition, if the timer value is additionally set to 5 hour, the control unit 130 may control the stimulation unit 120 to be maintained in an off state after the lapse of 5 hour from the maintenance of the stimulation unit 120 in the on state. As a second example using a timer, if the timer value is set to 01:00 am, the control unit 130 may control the stimulation unit 120 to be maintained in an off state before 01:00 am, and then control the stimulation unit 120 to be maintained in an on state after 01:00 am. In addition, if the timer value is additionally set to 05:00 am, the control unit 130 may control the stimulation unit 120 to be maintained in an off state after 05:00 am.

The communication unit 140 performs wired or wireless communication with an external device. For a first example, the external device may be a portable device. The portable device may be a smartphone, a notebook computer or a smart pad. For a second example, the external device may be a stationary device. The stationary device may be, for example, a personal computer, a server, other dedicated device for controlling and monitoring the brain-stimulating device 100. Through the communication unit 140, various items of information acquired from the stimulation unit 120 can be transmitted to the external device, and various items of control-related information can be transmitted to the control unit 130 and/or the stimulation unit 120.

Figure 3:
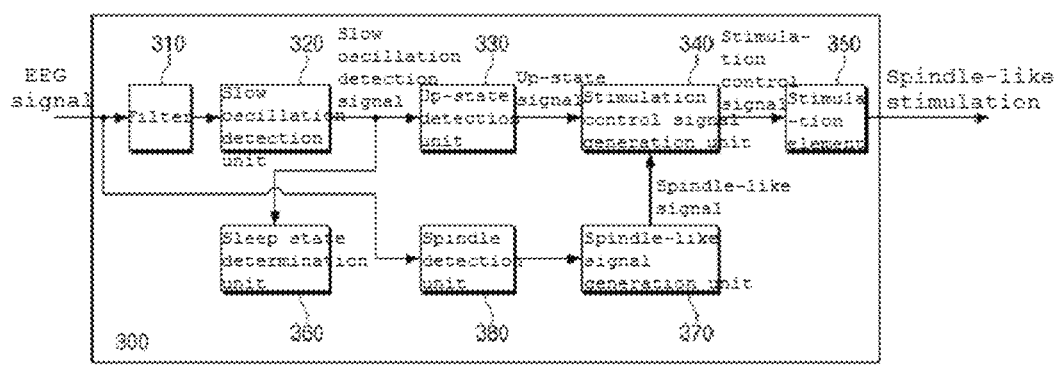
FIG. 3 is a block diagram showing an example of a configuration of a stimulation unit 120 shown in FIG. 1.
Figure 4:
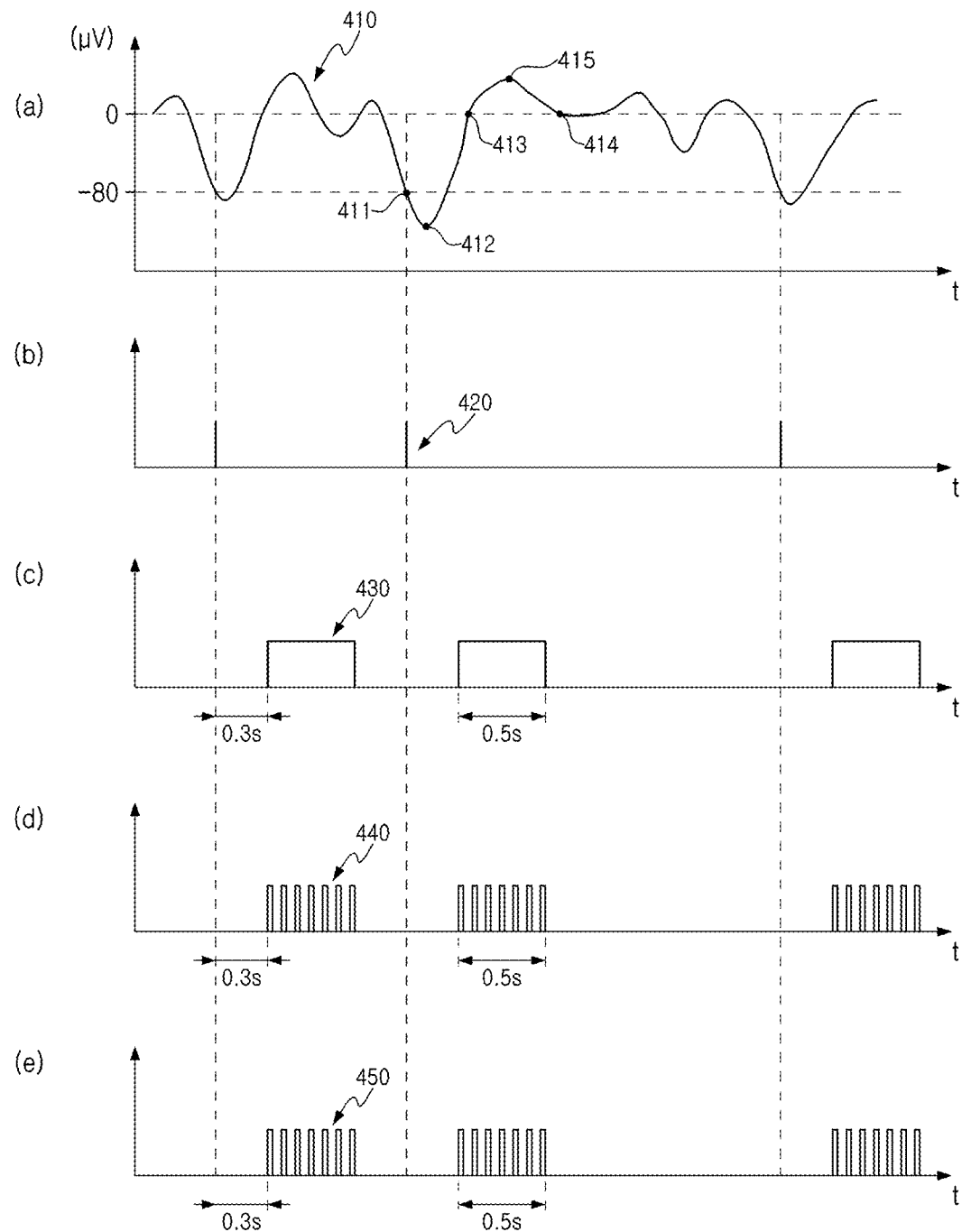

FIG. 3 is a block diagram showing an example of a configuration of a stimulation unit 120 shown in FIG. 1, and FIG. 4 is a view showing an example of signals included in FIG. 3. Referring to FIGS. 3 and 4, the stimulation unit 300 includes a filter 310, a slow oscillation detection unit 320, an up-state detection unit 330, a stimulation control signal generation unit 340, and a stimulation element 350. The stimulation unit 300 may further include a sleep state determination unit 360, a spindle-like signal generation unit 370, and a spindle detection unit 380.

The filter 310 receives an input of the EEG signal to allow a signal corresponding to a frequency band of the slow oscillation to pass therethrough. The EEG signal is transmitted from the EEG measurement unit 110 shown in FIG. 1. As a first example, the filter 310 may be a low pass filter. The cutoff frequency of the low pass filter may be 3.5 Hz. Alternatively, the cutoff frequency of the low pass filter may be a frequency selected from a range from 2 to 8 Hz. As a second example, the filter 310 may be a band pass filter. The lower cutoff frequency of the band pass filter may be within a range from 0.02 to 0.5 Hz, and the upper cutoff frequency thereof may be within a range from 2 to 8 Hz. An example of an EEG signal 410 having passed through the filter 300 is shown in FIG. 4(a).

The slow oscillation detection unit 320 detects the generation of the slow oscillation from an output signal 410 from the filter 310, and outputs a slow oscillation detection signal 420. For example, the low oscillation detection unit 320 determines that the slow oscillation is generated if the level of the EEG signal 410 having passed through the filter 310 is lower than or equal to a threshold value. The threshold value may be, for example, 80 μv. The threshold value may be changed depending on the input of a user or a manufacturer, or adaptively. An adaptive threshold value may be, for example, a value obtained by multiplying an average or a root means square (RMS) of the EEG signal 410 by a proportionality constant.

The up-state detection unit 330 outputs an up-state signal 430 corresponding to the up-state of the slow oscillation in response to the slow oscillation detection signal 420. As a first example, the up-state detection unit 330 starts the generation of the up-state signal when an event 413 occurs where the voltage of the slow oscillation is changed from negative one to positive one after the slow oscillation is detected, and ends the generation of the up-state signal when an event 414 occurs where the voltage of the slow oscillation is changed from positive one to negative one. As a second example, the up-state detection unit 330 starts the generation of the up-state signal after the slow oscillation is detected, a negative peak 412 of the slow oscillation occurs, and a first period is lapsed, and ends the generation of the up-state signal after the lapse of a second period, following the start of the up-state. As a third example, the up-state detection unit 330 starts the generation of the up-state signal after the slow oscillation is detected and a third period is lapsed, and ends the generation of the up-state signal after the lapse of a fourth period, following the start of the up-state. As a fourth example, the up-state detection unit 330 starts the generation of the up-state signal when the slow oscillation is detected, and then a positive peak 415 of the slow oscillation occurs, and ends the generation of the up-state signal when an event 414 occurs where the voltage of the slow oscillation is changed from positive one to negative one. The third example is shown in FIG. 4(c). The first to fourth periods may be fixed or variable values. As the variable values, values inputted by a user or a manufacturer, or the like may be used.

The stimulation control signal generation unit 340 generates a stimulation control signal 440 during the output of the up-state signal 430. The stimulation control signal 440 is shown as a square wave in FIG. 4(d), but may be modified variously. For example, the stimulation control signal may be a sine wave, a sawtooth wave, or a triangle wave.

The stimulation element 350 applies a spindle-like stimulation 450 to the brain in response to the stimulation control signal 440.

The sleep state determination unit 360 determines a sleep state based on the EEG signal or a signal induced from the EEG signal (e.g., the slow oscillation detection signal). As a first example, the sleep state determination unit 360 may determine whether or not the sleep state is a slow wave sleep state based on the frequency of generation (e.g., more than 20 times per minute) of the slow oscillation. To this end, the sleep state determination unit 360 may receive the slow oscillation detection signal from the slow oscillation detection unit 320. As a second example, the sleep state determination unit 360 may determine whether or not the sleep state is a slow wave sleep or an NREM sleep using various conventional techniques, and an example thereof includes a paper "Rechtschaffen A, Kales A. A manual of standardized terminology, techniques and scoring system for sleep stages of human subjects. Bethesda, Md.: US Department of Health, Education and Welfare, 1968." The sleep state determination unit 360 may further include an electromyography device (not shown) for determining the sleep state. The sleep state determination unit 360 turns on some of the stimulation unit 300 (e.g., the up-state detection unit 330, the stimulation control signal generation unit 340, stimulation element 350, the spindle-like signal generation unit 370, and the spindle detection unit 380) when the determined sleep state is the slow wave sleep. Otherwise, the sleep state determination unit 360 turns off some of the stimulation unit. In addition, the sleep state determination unit 360 turns on some of the stimulation unit 300 when the determined sleep state is the NREM sleep. Otherwise, the sleep state determination unit 360 turns off some of the stimulation unit.

The spindle-like signal generation unit 370 outputs a spindle-like signal having a spindle frequency. The spindle frequency may be, for example, within a range from 11 to 16 Hz. The output spindle-like signal is transmitted to the stimulation control signal generation unit 340, which in turn generates the stimulation control signal having the spindle frequency using the spindle-like signal. For example, the frequency of the spindle-like signal may have a fixed value (e.g., 13.5 Hz). For example, the frequency of the spindle-like signal may be changed adaptively to have the same frequency as that of the spindle included in the EEG signal. For example, the phase of the spindle-like signal may be determined to be the same as that of the spindle included in the EEG signal, and may be determined independently of the phase of the spindle. In order to allow the phase of the spindle-like signal to be the same as that of the spindle included in the EEG signal, the spindle-like signal generation unit 370 determines the phase of the spindle-like signal based on a signal corresponding to the EEG signal, which is transmitted from the spindle detection unit 380.

The spindle detection unit 380 detects a spindle included in the EEG signal. To this end, the spindle detection unit 380 may include a band pass filter that allows a signal corresponding to the spindle band from the EEG signal to pass therethrough. For example, the lower cutoff frequency of the band pass filter may be within a range from 8 to 11 Hz, and the upper cutoff frequency thereof may be within a range from 16 to 30 Hz. The frequency and/or phase of the spindle detected by the spindle detection unit 380 can be delivered to the spindle-like signal generation unit 370 so as to be used for the generation of the spindle-like signal. The spindle detection unit 380 can detect the induced spindle. For example, the induced spindle may be a spindle detected during a predetermined period from a time point when the spindle-like stimulation is ended. The predetermined period may be, for example, 0.3 sec. The predetermined period may be, for example, a value selected from 0.1 to 0.5 sec.

Figure 5:
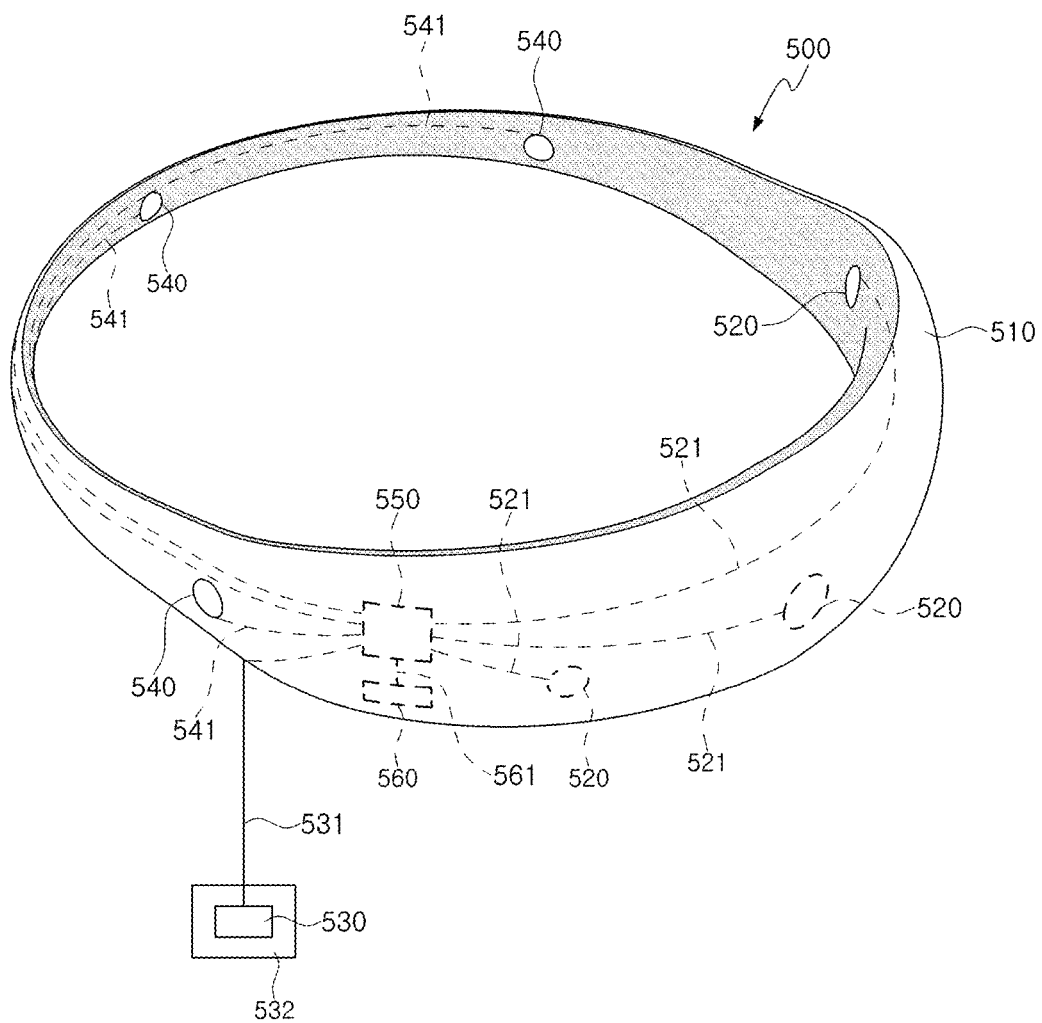
FIG. 5 is a view showing an example of a headband type implementation of the brain-stimulating device 100 shown in FIG. 1.

FIG. 5 is a view showing an example of a headband type implementation of the brain-stimulating device 100 shown in FIG. 1. Referring to FIG. 5, a brain-stimulating device 500 includes a headband 510, a plurality of measurement electrodes 520, a reference electrode 530, a plurality of ultrasonic generators 540, a control unit 550, and a communication unit 560.

The measurement electrodes 520 are disposed on the headband 510. The measurement electrodes 520 are in electrical contact with the forehead when the headband 510 is worn around the head of the subject. The measurement electrodes 520 are brought into close contact with the left, center and right sides of the forehead of a subject, respectively. Although three measurement electrodes 520 are shown in the drawing, some of the measurement electrodes 520 may be omitted. The measurement electrodes 520 are electrically connected to the processor 550 through wires 521.

The reference electrode 530 is separated from the headband 510. The reference electrode 530 is physically connected to the headband 510 through a wire 531, and is electrically connected to the processor 550. The reference electrode 530 may be adhered to the upper portion of the rear neck or an ear. The reference electrode 530 may be treated so that the surface thereof can be easily adhered to the skin.

The reference electrode 530 may be attached to the skin using an adhesive sheet 532. The measurement electrodes 520 and the reference electrode 530 correspond to the EEG measurement unit 110 of FIG. 1.

The ultrasonic generators 540 are disposed on the headband 510. The ultrasonic generators 540 emit ultrasonic waves toward the brain. The ultrasonic generators 540 are disposed on the left, right and rear sides of the brain, respectively. Although three ultrasonic generators 540 are shown in the drawing, some of the measurement electrodes 520 may be omitted. The ultrasonic generators 540 are electrically connected to the processor 550 through wires 541. The ultrasonic generators 540 may be, for example, a Piezo ultrasonic generator. As described above, any one selected from the group consisting of a speaker that can deliver sound to ears or the brain, an oscillation generator that can be brought into close contact with the scalp to provide oscillation, a magnetic electrode that can be electrically connected to the scalp to deliver electrical stimulation, a light source that can provide light to eyes or the brain, a coil that applies magnetic stimulation to the brain, and an antenna that applies electromagnetic wave stimulation to the brain may be disposed on the headband 510, in place of the ultrasonic generators 540. The ultrasonic generators 540 correspond to the stimulation element 350 of FIG. 3.

The processor 550 is electrically connected to the measurement electrodes 520, the reference electrode 530, the ultrasonic generators 540, and the communication unit 560. The processor 550 can perform some functions of the stimulation unit 120 of FIG. 1 (or the functions of the remaining constituent elements other than the stimulation element 350 in the stimulation unit 300) and the function of the control unit 130. For example, the processor 550 is implemented as a single hardware, but can be logically divided into the stimulation unit 120 and the control unit 130. For example, the processor 550 may include a hardware (e.g., a digital signal processor (DSP)) for the stimulation unit 120 and a hardware (e.g., a central processing unit (CPU) or a microprocessor) for the control unit 130. The processor 550 may further include an analog chip. The analog chip can perform amplification, filtering, analog-to-digital conversion (ADC), and the like.

The communication unit 560 performs a communication with an external portable device and/or a stationary device. The communication may be performed using any one of various communication methods including Wi-Fi, LTE and Zigbee. The communication unit 560 is electrically connected to the processor 550 through a wire 561. Unlike the drawing, the communication unit 560 may be omitted.

Figure 6:
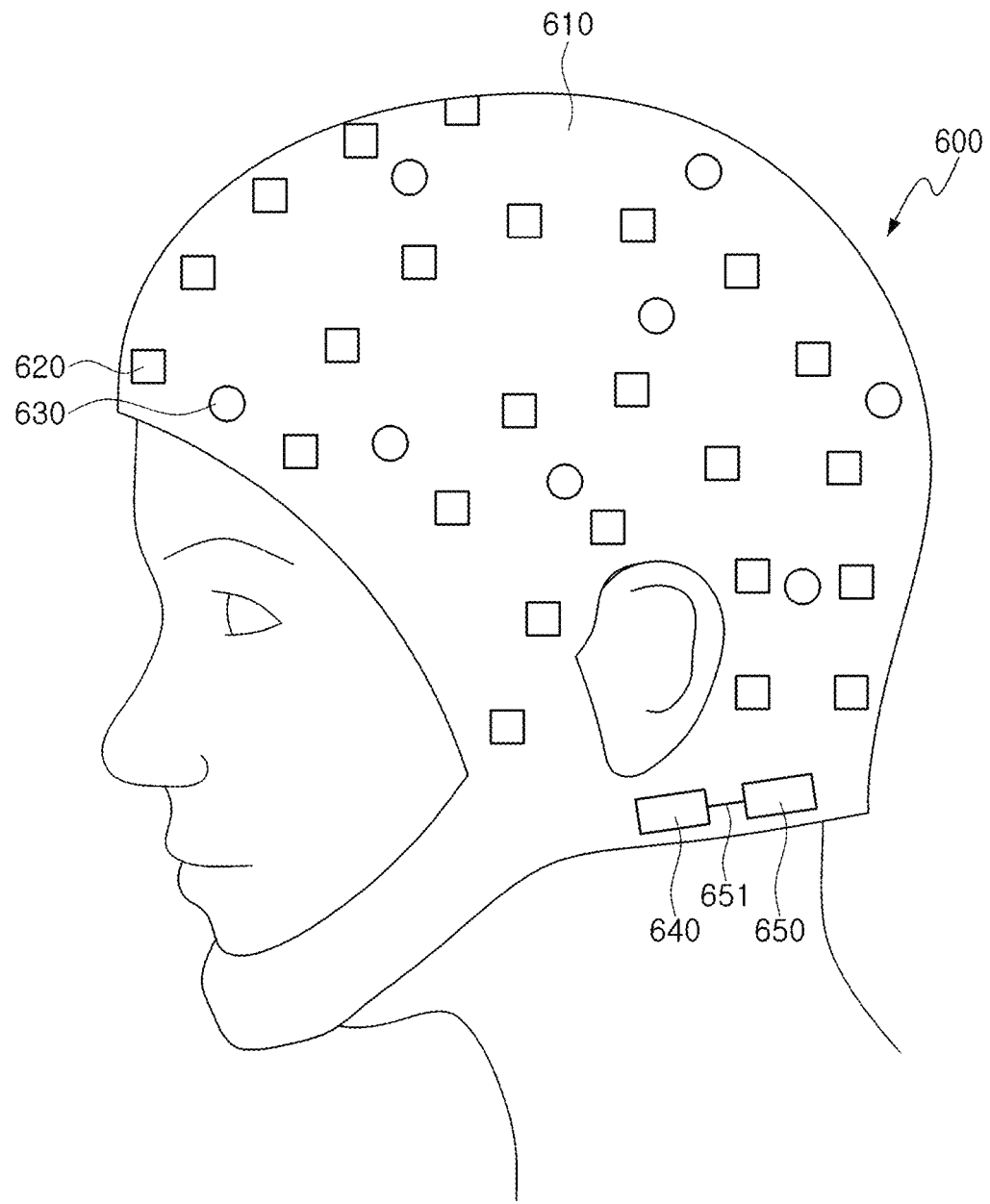
FIG. 6 is a view showing an example of a cap type implementation of the brain-stimulating device 100 shown in FIG. 1.

FIG. 6 is a view showing an example of a cap type implementation of the brain-stimulating device 100 shown in FIG. 1. Referring to FIG. 6, the brain-stimulating device 600 includes a cap 610, an electrode array 620, an ultrasonic generator array 630, a processor 640, and a communication unit 650.

The electrode array 620 is disposed on the cap 610. The electrode array 620 may be disposed according to the International 10-20 System of electrode placement, and may be disposed in a simpler manner. The electrode array 620 is electrically connected to the scalp. The electrode array 620 may be electrically connected to the scalp while being in direct contact with the scalp, and may be electrically connected to the scalp indirectly through a conductive gel or a hair. The electrode array 620 is electrically connected to the processor 640 through wires (not shown). The electrode array 620 corresponds to the EEG measurement unit 110 of FIG. 1.

The ultrasonic generator array 630 is disposed on a cap 610. The ultrasonic generator array 630 emits ultrasonic waves toward the brain. The ultrasonic generator array 630 is electrically connected to the processor 640 through a wire (not shown). The ultrasonic generator array 630 may be, for example, a Piezo ultrasonic generator. As described above, any one selected from the group consisting of a speaker that can deliver sound to ears or the brain, an oscillation generator that can be brought into close contact with the scalp to provide oscillation, a magnetic electrode that can be electrically connected to the scalp to deliver electrical stimulation, a light source that can provide light to eyes or the brain, a coil that applies magnetic stimulation to the brain, and an antenna that applies electromagnetic wave stimulation to the brain may be disposed on the cap 610, in place of the ultrasonic generator array 630. The ultrasonic generator array 630 corresponds to the stimulation element 350 of FIG. 3.

The processor 640 is electrically connected to the electrode array 620, the ultrasonic generator array 630 and the communication unit 650. The processor 640 can perform some functions of the stimulation unit 120 of FIG. 1 (or the functions of the remaining constituent elements other than the stimulation element 350 in the stimulation unit 300) and the function of the control unit 130. For example, the processor 640 is implemented as a single hardware, but can be logically divided into the stimulation unit 120 and the control unit 130. For example, the processor 640 may include a hardware (e.g., a digital signal processor (DSP)) for the stimulation unit 120 and a hardware (e.g., a central processing unit (CPU) or a processor) for the control unit 130. The processor 640 may further include an analog chip. The analog chip can perform amplification, filtering, analog-to-digital conversion (ADC), and the like.

The communication unit 650 performs a communication with an external portable device and/or a stationary device. The communication may be performed using any one of various communication methods including Wi-Fi, LTE and Zigbee. The communication unit 650 is electrically connected to the processor 640 through a wire 651. Unlike the drawing, the communication unit 650 may be omitted.

Figure 7:
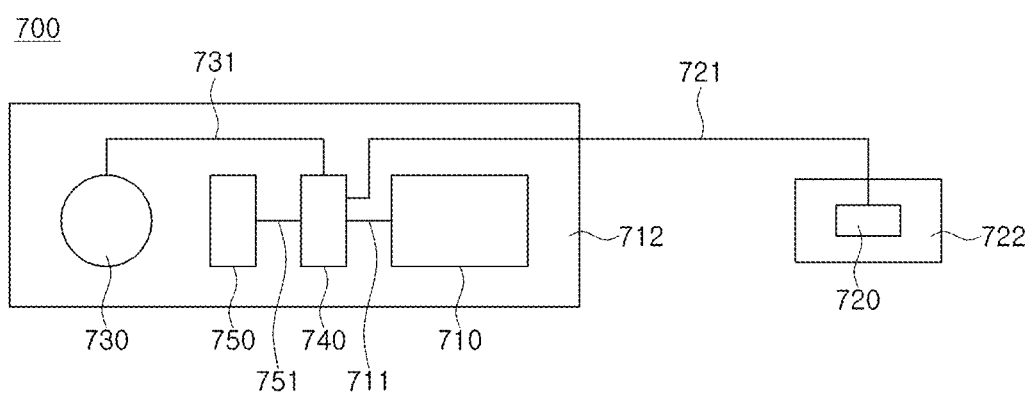
FIG. 7 is a view showing an example of an adhesion type implementation of the brain-stimulating device 100 shown in FIG. 1.

FIG. 7 is a view showing an example of an adhesion type implementation of the brain-stimulating device 100 shown in FIG. 1. Referring to FIG. 7, a brain-stimulating device 700 includes a measurement electrode 710, a reference electrode 720, a stimulation element 730, a processor 740, and a communication unit 750.

The reference electrode 710 may be adhered to the scalp. As a first example, the reference electrode 710 may be attached to the scalp using an adhesive sheet 712 as shown in the drawing. As a second example, the reference electrode 710 may be treated so that the surface thereof can be easily adhered to the skin unlike the drawing. The measurement electrode 710 is electrically connected to the processor 740 through a wire 711.

The reference electrode 720 may be adhered to a scalp, the upper portion of a rear neck or an ear. As a first example, as shown in the drawing, the reference electrode 720 may be adhered using an adhesive sheet 722. As a second example, unlike the drawing, the reference electrode 720 may be treated so that the surface thereof can be easily adhered to the skin. The reference electrode 720 is electrically connected to the processor 740 through a wire 721. The measurement electrode 710 and the reference electrode 720 correspond to the EEG measurement unit 110 of the FIG. 1.

The stimulation element 730 is electrically connected to the processor 740 through a wire 731. As shown in the drawing, the stimulation element 730 may be disposed on an adhesive sheet 712 for the measurement electrode. In addition, unlike the drawing, the stimulation element 730 may be disposed on an adhesive sheet 722 for the reference electrode or a separate adhesive sheet. The stimulation element 730 corresponds to the stimulation element 350 of FIG. 3.

The processor 740 is electrically connected to the measurement electrode 710, the reference electrode 720, the stimulation element 730, and the communication unit 750. As shown in the drawing, the processor 740 may be disposed on an adhesive sheet 712 for the measurement electrode. In addition, unlike the drawing, the processor 740 may be disposed on an adhesive sheet 722 for the reference electrode or a separate adhesive sheet. The processor 740 can perform some functions of the stimulation unit 120 of FIG. 1 (or the functions of the remaining constituent elements other than the stimulation element 350 in the stimulation unit 300) and the function of the control unit 130. For example, the processor 740 is implemented as a single hardware, but can be logically divided into the stimulation unit 120 and the control unit 130. For example, the processor 740 may include a hardware (e.g., a digital signal processor (DSP)) for the stimulation unit 120 and a hardware (e.g., a central processing unit (CPU) or a processor) for the control unit 130. The processor 740 may further include an analog chip. The analog chip can perform amplification, filtering, analog-to-digital conversion (ADC), and the like.

The communication unit 750 performs a communication with an external portable device and/or a stationary device. The communication may be performed using any one of various communication methods including Wi-Fi, LTE and Zigbee. The communication unit 750 is electrically connected to the processor 740 through a wire 751. As shown in the drawing, the communication unit 750 may be disposed on an adhesive sheet 712 for the measurement electrode. In addition, unlike the drawing, the communication unit 750 may be disposed on an adhesive sheet 722 for the reference electrode or a separate adhesive sheet. Unlike the drawing, the communication unit 750 may be omitted.

Figure 8:
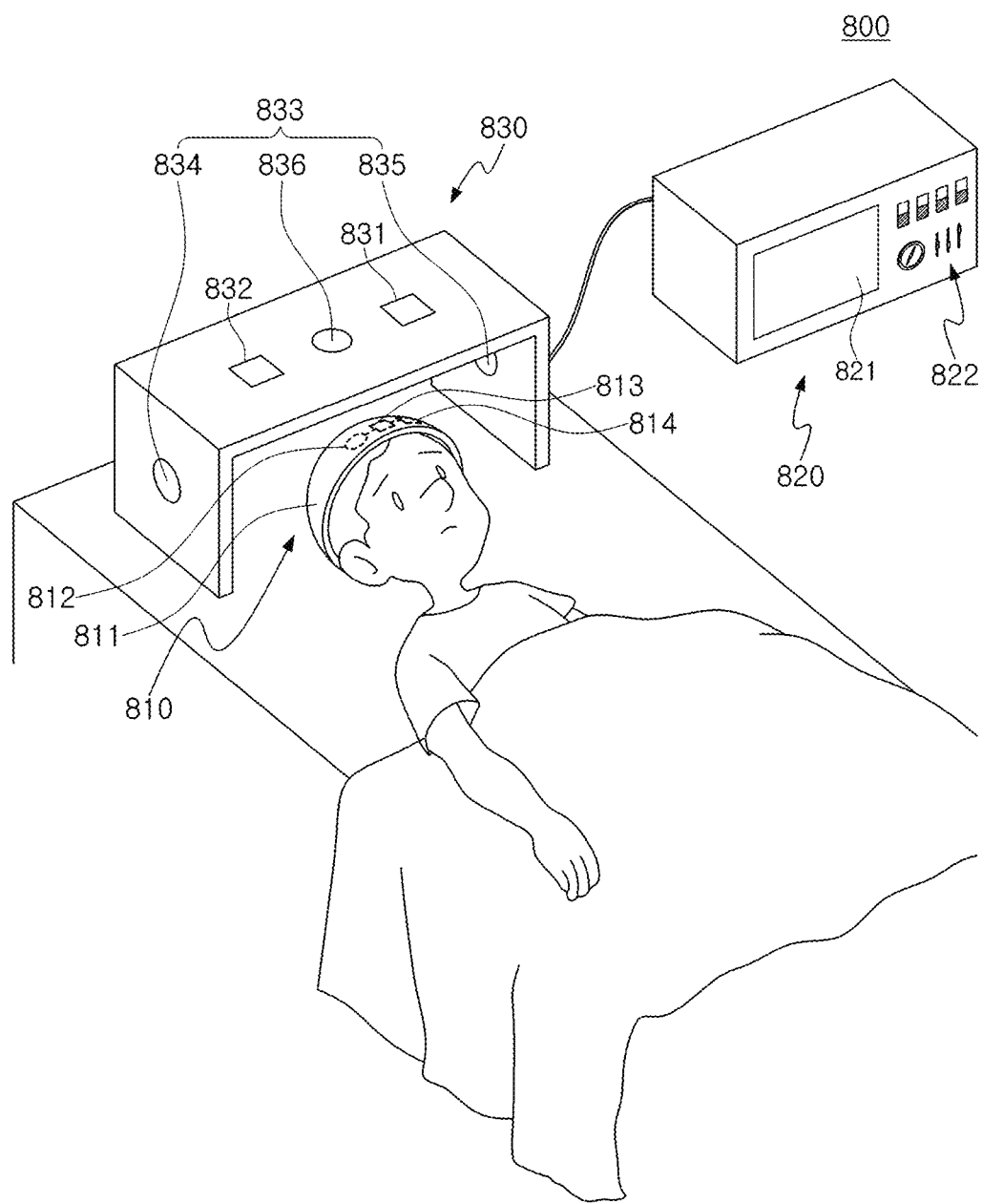
FIG. 8 is a view showing an example of a system type implementation of the brain-stimulating device 100 shown in FIG. 1.

FIG. 8 is a view showing an example of a system type implementation of the brain-stimulating device 100 shown in FIG. 1. Referring to FIG. 8, a brain-stimulating device 800 includes an EEG measurement module 810, a signal processing module 820, and a stimulation module 830.

The EEG measurement module 810 includes a cap 811, at least one electrode 812, an analog signal processing unit 813, and a communication unit 814. EEG signals measured from the electrode 812 disposed on the cap 811 is transmitted to the signal processing module 820 via the analog signal processing unit 813 and the communication unit 814. The analog signal processing unit 813 performs amplification, filtering, analog-to-digital conversion (ADC), and the like. The communication unit 814 transmits the digital converted signal to the signal processing module 820. Although it has been illustrated in the drawing that the EEG signal is transmitted wirelessly, the EEG signal may be transmitted wiredly unlike the drawing. A headband or other item may be used instead of the cap 811. A digital signal processing unit (not shown) may be electrically connected between the analog signal processing unit 813 and the communication unit 814.

Figure 11:
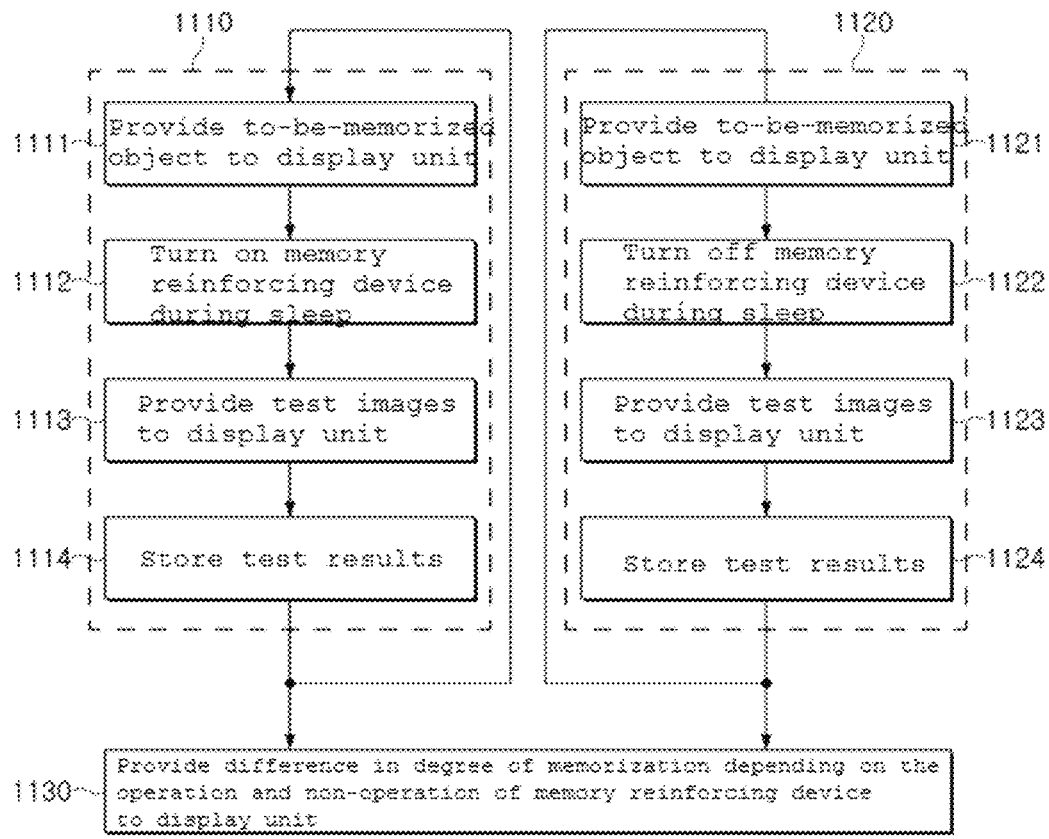
FIG. 11 is a view showing a process for assessing the performance of the brain-stimulating device according to the present invention.

The signal processing module 820 includes a central processing unit (CPU) (not shown), a display unit 821, an input unit 822, and a communication unit (not shown). The CPU performs some functions of the stimulation unit 120 of FIG. 1. The remaining functions of the stimulation unit 120 of FIG. 1 can be performed by the EEG measurement module 810 and the stimulation module 830. The CPU may additionally perform the function of the control unit 130 of FIG. 1, and the function of the processor 920 of FIG. 9. The display unit 821 can display one or more selected from among a digital converted EEG signal, a measured slow oscillation, a measured spindle, a spindle-like signal applied to the brain, sleep stages (REM sleep, NREM sleep stage 1, NREM sleep stage 2 and NREM sleep stage 3, NREM sleep stage 4, slow wave sleep, etc.), presence or absence of NREM sleep, an NREM sleep period, presence or absence of slow wave sleep, a slow wave sleep period, the frequency of generation of a slow oscillation, the intensity of a spindle-like signal, a degree in which a spindle-like stimulation is applied, and a degree in which a spindle is induced to a brain by the spindle-like stimulation. The input unit 822 may include one or more selected from among an input means for controlling the intensity of a spindle-like stimulation, an input means for controlling the phase difference between a slow oscillation component of the spindle-like stimulation and a slow oscillation included an EEG signal, an input means for controlling the on/off operation of the EEG measurement module 810, and an input means for controlling the on/off operation of the stimulation module 830. The input unit 822 may be, for example, a touch input unit. The CPU can perform the performance assessment of the brain-stimulating device as shown in FIG. 11 in cooperation with the display unit 821 and the input unit 822. The communication unit performs communications between the signal processing module 820 and the EEG measurement module 810, and between the signal processing module 820 and the stimulation module 830. For example, the signal processing module 820 and the EEG measurement module 810 can perform communications therebetween wirelessly, and the signal processing module 820 and the stimulation module 830 can perform communications therebetween wiredly.

The stimulation module 830 includes a communication unit 831, a position recognition unit 832, and one or more stimulation elements 833. The communication unit 831 performs a communication with the signal processing module 820. The position recognition unit 832 recognizes the position of a brain or a head. As a first example, the position recognition unit 832 includes a infrared light emitting element (IR LED) and an infrared camera, and recognizes the position of the brain through image processing of a captured image. As a second example, the position recognition unit 832 includes a thermal imaging camera, and recognizes the position of the brain through image processing of a captured image. As a third example, the position recognition unit 832 receives a signal (e.g., an infrared signal, an ultrasonic signal, or the like) from the EEG measurement module 810 through one or more receivers, and recognizes the position of the brain or the EEG measurement module 810 using the received signal. To this end, the EEG measurement module 810 includes one or more transmitters (not shown). The stimulation element 833 applies stimulation in response to a stimulation control signal transmitted from the signal processing module 820 via the communication unit 831. The stimulation element 833 includes one or more stimulation sources, for example, left, right and upper stimulation sources 834, 835 and 836. The stimulation element 833 changes a stimulation position depending on the recognized brain position. As a first example of changing the stimulation position, the stimulation sources 834, 835 and 836 have directivity and change a stimulation direction depending on the recognized position of the brain. The stimulation sources 834, 835 and 836 having directivity may be a focused ultrasound device. As a second example of changing the stimulation position, the stimulation sources 834, 835 and 836 are omnidirectional stimulation sources. When the position of the brain is adjacent to the left stimulation source 834, the intensity of stimulation of the left stimulation source 834 is reinforced, but the intensity of stimulation of the right stimulation source 835 is weakened.

In another aspect, the present invention is directed to a portable device configured to be operated in cooperation with the brain-stimulating device, the portable device comprising a communication unit configured to perform communication with the brain-stimulating device; and a touch display unit, wherein the touch display unit displays any one of selected from the group consisting of an image necessary for controlling the intensity of spindle-like stimulation; an image necessary for controlling the phase difference between a slow oscillation component of the spindle-like stimulation and slow oscillation included in an EEG signal; and an image necessary for controlling the on/off operation of the brain-stimulating device.

In another aspect, the present invention is directed to a portable device configured to be operated in cooperation with the brain-stimulating device, the portable device comprising: a communication unit configured to perform communication with the brain-stimulating device; and a display unit, wherein the touch display unit displays any one of selected from the group consisting of a degree in which a spindle-like stimulation is applied; a degree in which a spindle is induced to a brain by the spindle-like stimulation; and a degree in which the brain-stimulating device is operated.

Figure 9:
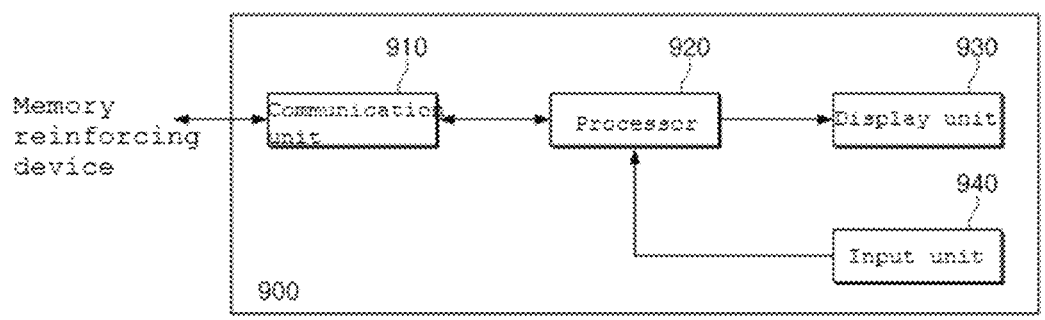
FIG. 9 is a block diagram showing an example of a configuration of a portable device 900 configured to be operated in cooperation with the brain-stimulating device 100 shown in FIG. 1.

FIG. 9 is a block diagram showing an example of a configuration of a portable device 900 configured to be operated in cooperation with the brain-stimulating device 100 shown in FIG. 1. Referring to FIG. 9, a portable device 900 includes a communication unit 910, a processor 920, a display unit 930, and an input unit 940. The communication unit 910 performs a communication with the brain-stimulating device 100. The processor 920 controls the operation of the communication unit 910 and the display unit 930, and controls the brain-stimulating device 100 via the communication unit 910. The processor 920 performs various calculations based on information transmitted from the input unit 940 and the brain-stimulating device 100. The display unit 930 displays images under the control of the processor 920. The input unit 940 transmits an input of a user to the processor 920. The input unit 940 may be, for example, a touch input unit. The portable device 900 may be, for example, a smartphone, a smart pad or a notebook computer.

Figure 10:
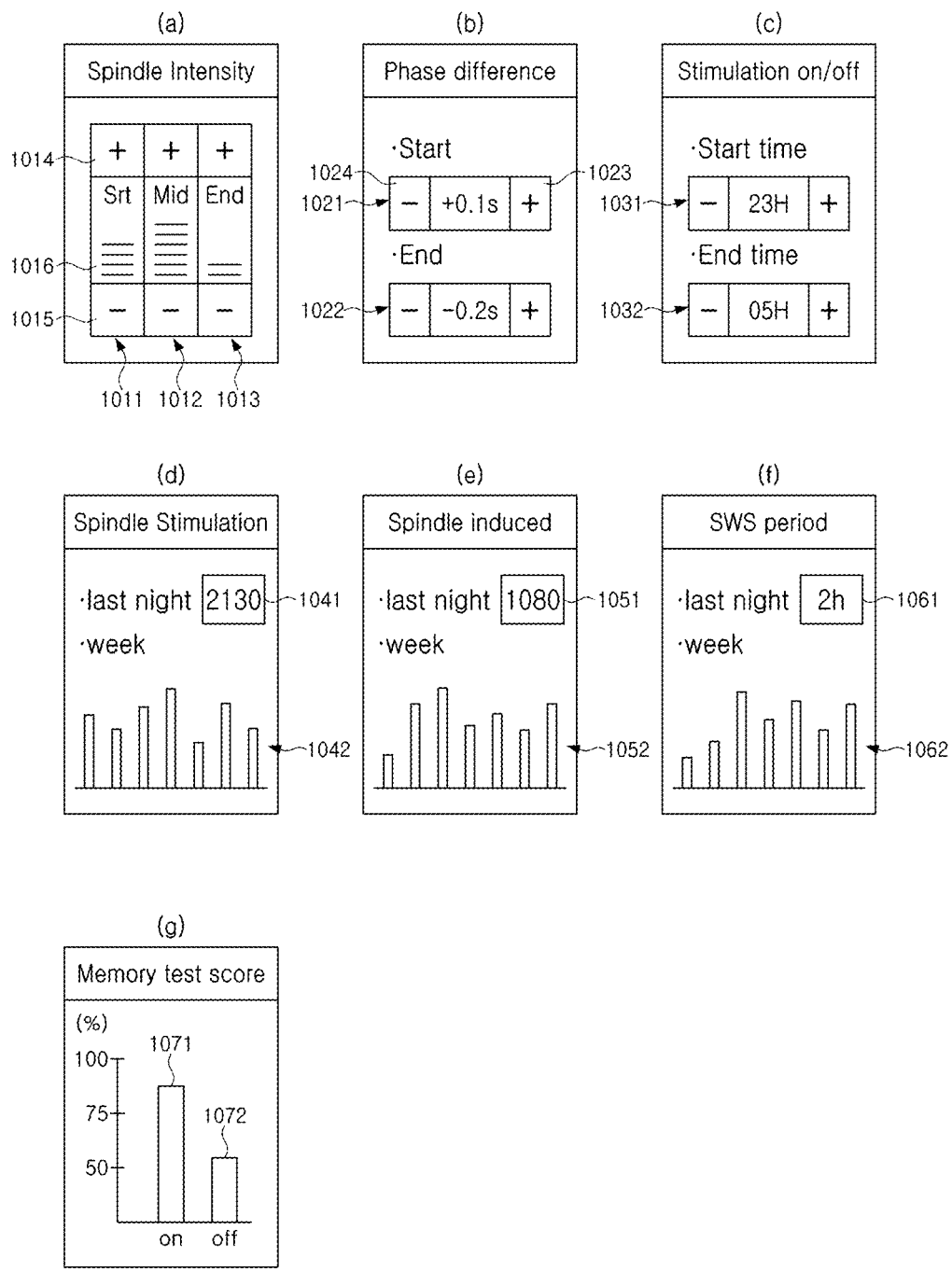
FIG. 10 is a view showing examples of a screen of a display unit 930 shown in FIG. 9.

FIG. 10 is a view showing examples of a screen of a display unit 930 shown in FIG. 9. FIG. 10(*a*) shows a screen for control of the intensity of the spindle-like stimulation. In FIG. 10(*a*), reference numerals 1011, 1012 and 1013 denote screens for control of the intensities of the spindle-like stimulation at an initial stage, an intermediate stage and a final stage of the sleep period, respectively. In the screens, the intensity of the spindle-like stimulation can be controlled by touching a "+" region 1014 or a "−" region 1015. A reference numeral 1016 denotes a region where the intensity of the spindle-like stimulation is displayed using the number of bars. Although it has been illustrated in the drawing that the intensity of the spindle-like stimulation is controlled using the sleep period divided into three periods, the sleep period may be one period or may be divided into two or three or more periods unlike the drawing.

FIG. 10(*b*) shows a screen for control of the phase difference between the slow oscillation component of the spindle-like stimulation and the slow oscillation included in the EEG signal. In FIG. 10(*b*), reference numerals 1021 and 1022 denote screens for control of the start and end time points of the slow oscillation component, respectively. In the screens, when a "+" region 1023 is touched, the start time point or the end time point is changed to be increased, and when a "−" region is touched, the start time point or the end time point is changed to be decreased.

FIG. 10(*c*) shows a screen for control of the on/off operation of the brain-stimulating device 100. In FIG. 10(*c*), reference numerals 1031 and 1032 denote screens for control of the ON time and OFF time of the brain-stimulating device 100, respectively. In FIG. 10(*c*), the brain-stimulating device 100 is partially or entirely turned on and off at 23:00 pm and 05:00 am, respectively.

The intensity of the spindle-like stimulation, the phase difference between the slow oscillation component of the spindle-like stimulation and the slow oscillation included in the EEG signal, and the on/off time of the brain-stimulating device, as determined from the screens of FIGS. 10(*a*) to (*c*), are transmitted to the brain-stimulating device 100 via the processor 920 and the communication unit 910.

FIG. 10(*d*) shows a degree in which the spindle-like stimulation is applied. In FIG. 10(*d*), reference numerals 1041 and 1042 denote a degree in which the spindle-like stimulation is applied last night and during one week, respectively. For example, the degree of application of the spindle-like stimulation may be the frequency of generation of the slow oscillation component of the spindle-like stimulation. For example, the degree of application of the spindle-like stimulation may be determined depending on at least one selected from among the frequency of generation of the slow oscillation component, the intensity of the spindle-like stimulation, and the duration of the slow oscillation component.

FIG. 10(*e*) shows a degree in which a spindle is induced to a brain by the spindle-like stimulation. Referring to FIG. 10(*e*), reference numerals 1051 and 1052 denote the degree in which the spindle is induced last night and during one week, respectively. For example, the degree of induction of the spindle may be determined depending on at least one selected from among the number of spindles induced, the intensity of the induced spindle, and the period during which the spindle is induced.

FIG. 10(*f*) shows a slow wave sleep period. Referring to FIG. 10(*f*), reference numerals 1061 and 1062 denote the slow wave sleep period last night and during one week, respectively.

In order for various items of information to be displayed on a screen as shown in FIGS. 10(*d*) to 10(*f*), these items of information should be transmitted to the display unit 930 from the brain-stimulating device 100 via the communication unit 910 and the processor 920.

FIG. 10(*g*) shows a difference in the degree of memorization according to the presence or absence of the operation of the brain-stimulating device. This drawing will be described later with reference to FIG. 11.

In still another aspect, the present invention is directed to a method for assessing the performance of a brain-stimulating device, the method comprising: (a) providing an object to be memorized of a user to the touch display unit of the portable device of the present invention before sleep; (b) turning on or off the brain-stimulating device during sleep; and (c) performing a step of providing a screen for testing a degree of memorization of the to-be-memorized object of the user after sleep, several times, then displaying a difference in the degree of memorization according to the on or off operation of the brain-stimulating device.

FIG. 11 is a view showing a process for assessing the performance of the brain-stimulating device according to the present invention. Referring to FIG. 11, the portable device stores memorization test results when the brain-stimulating device is operated (1110). To this end, the portable device displays an object to be memorized (or to-be-memorized object) on the display unit before sleep (1111), operates the brain-stimulating device during sleep (1112), displays test images on the display unit after sleep (1113), and stores memory test results after test (1114).

The portable device stores memory test results when the brain-stimulating device is not operated (1120). To this end, the portable device displays the to-be-memorized object on the display unit before sleep (1121), does not operate the brain-stimulating device during sleep (1122), displays test images on the display unit after sleep (1123), and stores memory test results after test (1124).

The portable device performs the steps corresponding to reference numerals 1110 and 1120 multiple times, and then displays, on the display unit, a difference in the degree of memorization depending on the operation and non-operation of the brain-stimulating device (1130). A screen of displaying the difference in the degree of memorization depending on the operation and non-operation of the brain-stimulating device is shown in FIG. 10(g). Referring to FIG. 10(g), reference numerals 1071 and 1072 denote test scores upon the operation and non-operation of the brain-stimulating device, respectively.

In yet another aspect, the present invention is directed to a method for enhancing memory, the method comprising: (a) providing an object to be memorized to a user before sleep; and (b) stimulating a brain using the brain-stimulating device during sleep.

As mentioned above, the inventors of this application have demonstrated that when an artificial spindle-like signal is applied to the brain, a substantial spindle is induced to the brain, and that the induced substantial spindle reinforces a memory (e.g., hippocampus-dependent memory). Based on this demonstration, research and development are conducted, which in turn leads to completion of the present invention. Hereinafter, the experiments performed by the inventors of the present invention will be described for reference.

Example 1: Confirmation of Effect of Spindle Stimulation By Contextual Fear Conditioning and Position Recognition Assessment A spindle-like stimulation in-phase with slow oscillation up-states enhances memory.

The present inventors conducted a combined cued/contextual fear-conditioning (FC) test using transgenic mice expressing channelrhodopsin2 (ChR2) in parvalbumin (Prv)-expressing inhibitory neurons (PrvmhChR2-EYFP; n=26), a dominant subpopulation of the TRN that is sparse in surrounding thalamic nuclei.

Figure 12:
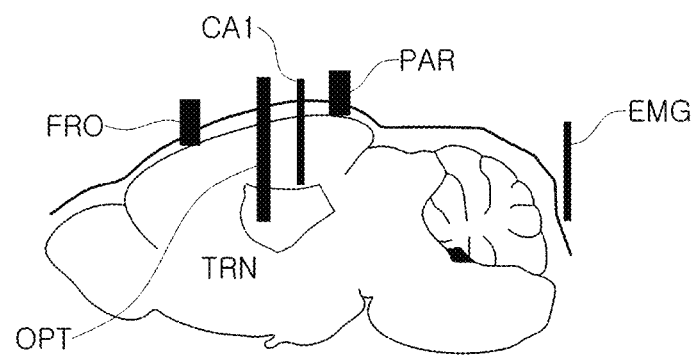
FIG. 12 is a view showing positions where electrodes and an optical fiber cannula are arranged in a mouse brain in an experiment.

As shown in FIG. 12, in order to apply optogenetic stimulation to a brain and measure EEGs, four electrodes (FRO, PAR, CA1, EMG) and an optical fiber cannula (OPT) are arranged on a mouse brain. The four electrodes (FRO, PAR, CA1, EMG) include an electrode (FRO) for measuring a prefrontal cortex EEG, an electrode (PAR) for measuring a parietal lobe EEG, an electrode (CA1) for measuring a local field potential, and an electrode (EMG) for electromyography. The optogenetic stimulation is applied to the thalamic reticular nucleus (TRN) through the optical fiber cannula (OPT).

Figure 13:
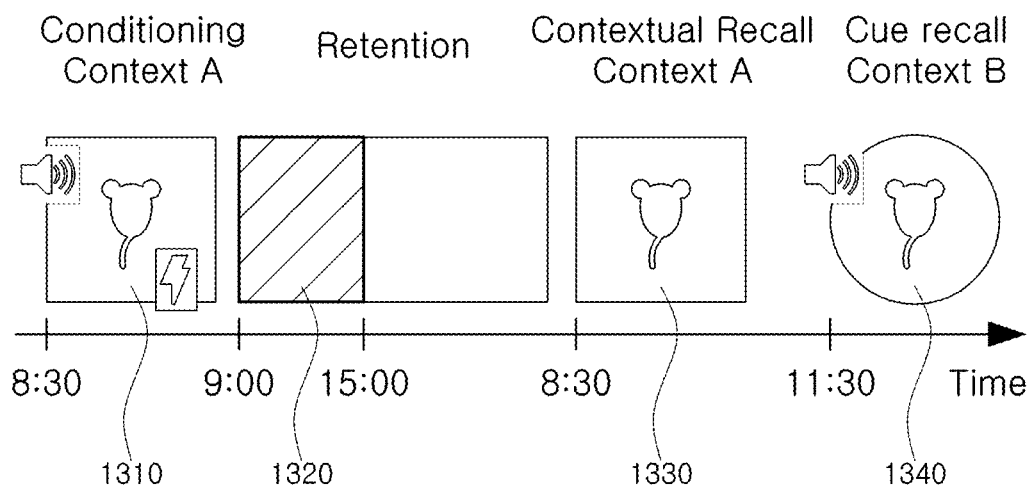
FIG. 13 is a view showing a cue/context fear conditioning experimental procedure.
Figure 14:
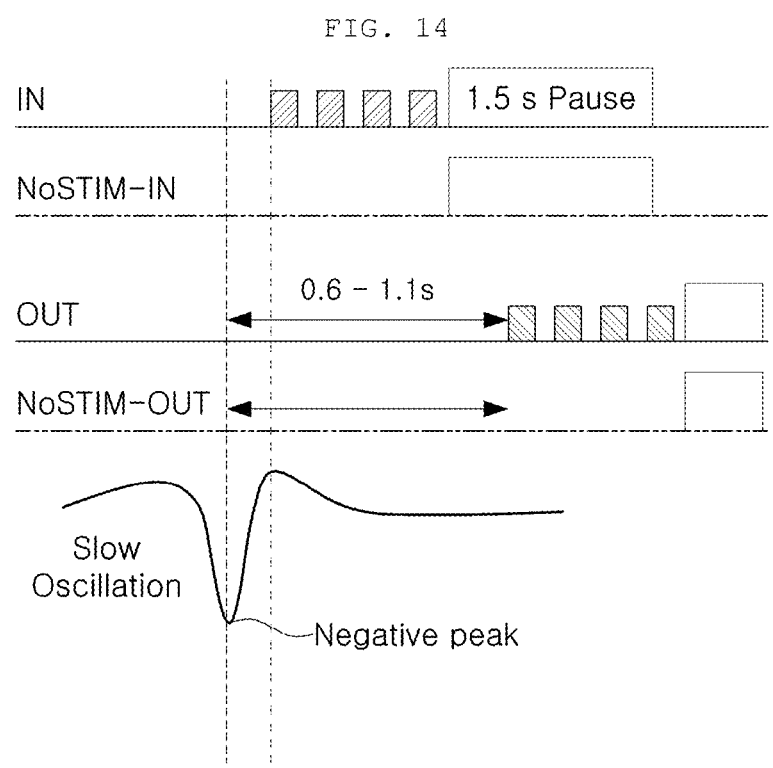
FIG. 14 is a view showing in-phase stimulation, out-of-phase stimulation, and no-stimulation, which are applied to a mouse brain.

As shown in FIG. 13, fear conditioning was performed in such a manner that a tone as a signal followed by a shock was delivered to mice as in context A (1310). Following the fear conditioning test, mice were subjected to one of three stimulation protocols for 6 hr as shown in FIG. 14 (1320). 24 hours later, at the memory recall or retrieval step, (i) the frozen behavior of the mouse was observed and evaluated in context A like hippocampus recording, to read the context-dependent fear memory (1330), (ii) the frozen behavior of the mouse was evaluated by giving a tone as a signal in the other situation B for the reading of fear memory by a signal that is not dependent on the hippocampus (1340).

Figure 15:
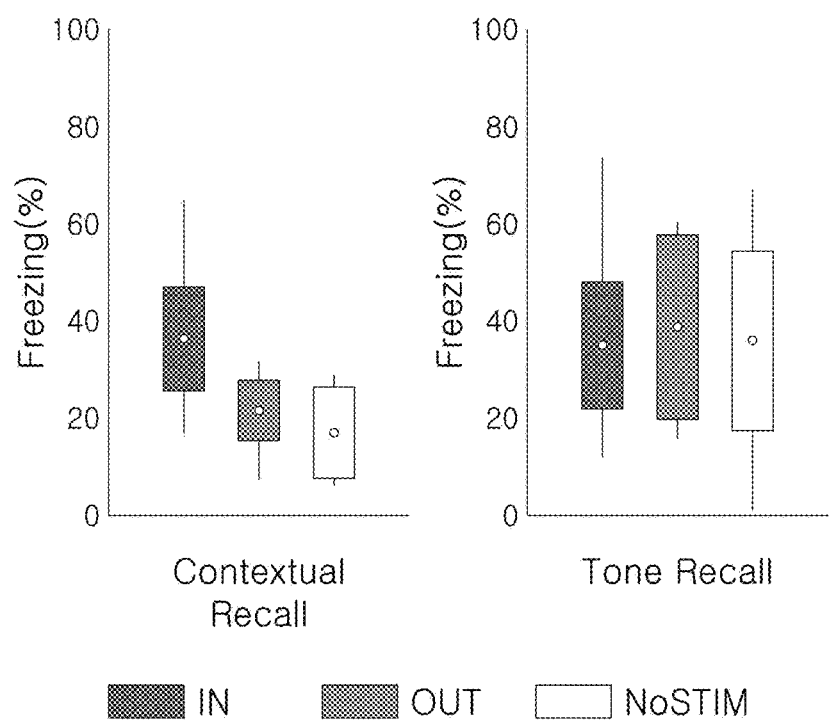
FIG. 15 is a view showing a degree of contextual recall and tone recall in a memory recall or retrieval step.

For the sake of convenience of explanation, optogenetic stimulation occurred during a slow oscillation up-state is referred to as "in-phase stimulation", and mice having received the in-phase stimulation are referred to as "in-phase mice". In addition, optogenetic stimulation with a random delay between 0.6 and 1.1 sec at a negative peak of slow oscillation is referred to as "out-of-phase stimulation", and mice having received the out-of-phase stimulation are referred to as "out-of-phase mice". In-phase mice (IN) received spindle-like optogenetic stimulation to the TRN during NREM sleep, which occurred in synchrony with the up-states of online (i.e., in real time from the brain)-detected slow oscillations. Out-of-phase mice (OUT) were likewise stimulated during NREM sleep but with a random delay between 0.6 and 1.1 sec following identification of a slow oscillation up-state. As shown in FIG. 14, four light pulses (8 Hz, 62.5 ms on/off) having a spindle-like frequency were used for optogenetic stimulation. Control mice (NoSTIM-IN, NoSTIM-OUT) received no stimulation (NoSTIM). As a result of the experiment, it was confirmed that at retrieval, contextual fear memory was enhanced in in-phase mice (IN), whereas out-of-phase mice (OUT) showed no improvement in contextual fear memory compared with no-stimulation controls (NoSTIM) (FIG. 15). Collectively, these results demonstrate that spindles are not effective per se, but instead enhance hippocampus-dependent memory only if they coincide with the up-state of a slow oscillation. Neither in-phase (IN) nor out-of-phase (OUT) stimulation changed memory for cued fear compared with that observed in no-stimulation (NoSTIM) control mice, indicating that stimulation in-phase during NREM sleep preferentially benefits hippocampus-dependent memory.

Example 2: Confirmation of Intensity of Spindle by Sleep Stage Depending on Stimulation An increase in the correlation between the slow oscillations and the spindles leads to an increase in contextual memory without any change in sleep structure.

The effects of in-phase stimulation on memory formation were not conveyed by gross changes in sleep structure. Sleep onset and time spent in different sleep stages during the 6-hour interval were closely comparable among the three stimulation conditions (Table 1). In addition, the overall density of slow oscillation, spindle, and ripple events did not differ among conditions (Table 2).

TABLE 1

|  | In-phase | Out-of-phase | No-stimulation | One-way ANOVA $F_{2.26}$ | P |
|---|---|---|---|---|---|
| Sleep onset (min) | 18.4 ± 3.4 | 13.6 ± 2.1 | 25.3 ± 5.4 | $U_2$ = 0.705 | 0.703 |
| Wake (min) | 116.5 ± 9.4 | 126.7 ± 7.1 | 133.2 ± 5.6 | 0.156 | 0.857 |
| NREM (min) | 169.1 ± 11.3 | 189.1 ± 5.7 | 179.1 ± 5.4 | $U_2$ = 0.560 | 0.756 |
| REM (min) | 23.2 ± 1.7 | 24.5 ± 0.9 | 24.5 ± 1.1 | $U_2$ = 4.319 | 0.115 |

TABLE 2

|  |  | In-Phase | Out-of-Phase | No-Stimulation | One-way ANOVA $F_{2, 26}$ | P |
|---|---|---|---|---|---|---|
| Slow oscillations | FRO | 37.82 ± 0.86 | 39.64 ± 0.52 | 37.88 ± 0.79 | 1.8404 | 0.185 |
|  | PAR | 38.58 ± 0.87 | 39.76 ± 0.78 | 38.92 ± 0.69 | 0.580 | 0.567 |
| Spindles | FRO | 5.42 ± 0.13 | 5.33 ± 0.08 | 5.11 ± 0.10 | 2.567 | 0.096 |
|  | PAR | 6.83 ± 0.22 | 6.96 ± 0.21 | 6.65 ± 0.23 | 0.513 | 0.605 |
|  | CA1 | 5.25 ± 0.35 | 5.11 ± 0.20 | 5.25 ± 0.35 | 0.058 | 0.944 |
| Ripples | CA1 | 22.18 ± 1.50 | 19.56 ± 1.20 | 23.01 ± 1.26 | 3.397* | 0.183 |

Figure 16:
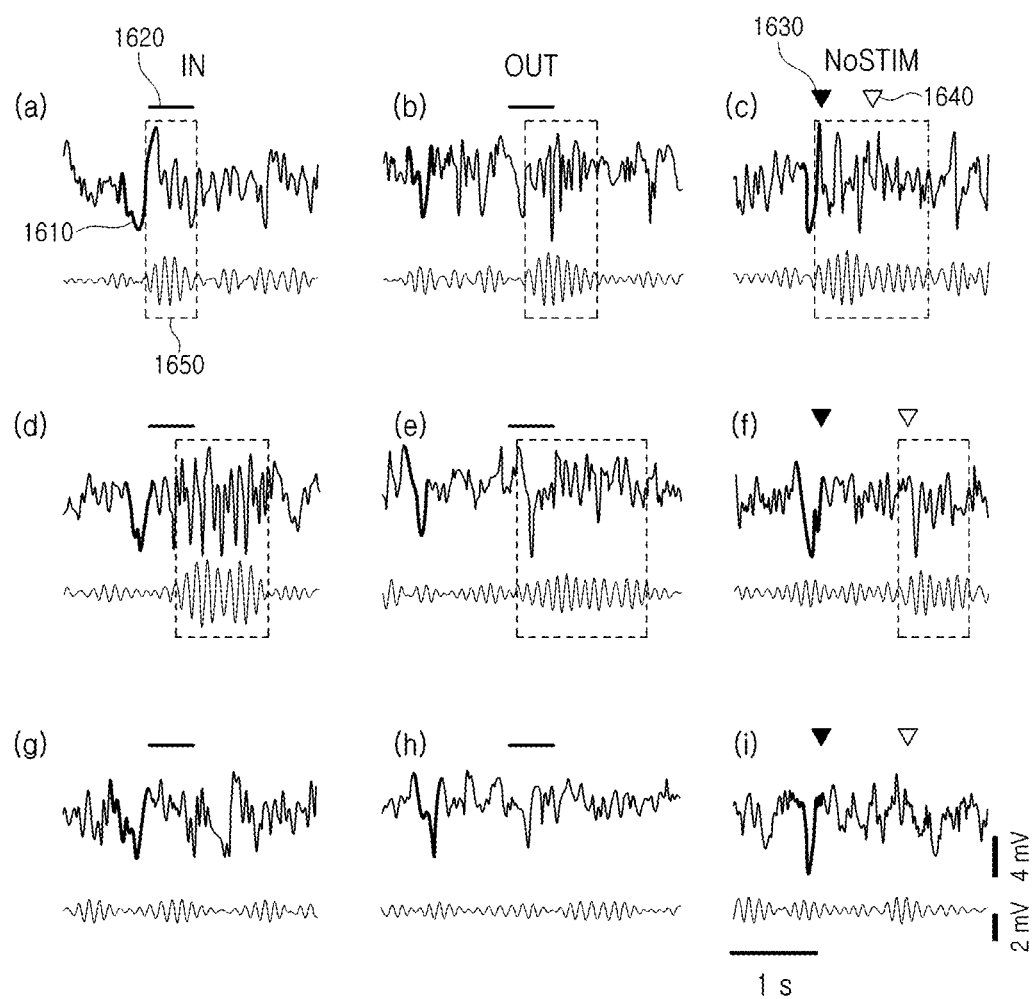
FIG. 16 is a result of measuring representative prefrontal cortex EEG (PFC-EEG) appearing when spindle-like stimulation is applied, wherein FIG. 16(a), FIG. 16(d) and FIG. 16 (g) are in-phase stimulations, FIG. 16(b), FIG. 16(e) and FIG. 16 (h) are out-of-phase stimulations, and FIG. 16(c), FIG. 16(f) and FIG. 16 (i) are no-stimulations.

However, optogenetic spindle stimulation altered the fine-tuned interaction between the three rhythms (FIG. 16). FIG. 16 shows three representative prefrontal cortex EEG (PFC-EEG) traces for each of the three experimental protocols (i.e., in-phase((a), (d), (g)), out-of-phase((b), (e), (h)) and no-stimulation((c), (f), (i))). The top two rows ((a) to (f)) show examples with application of spindle, whereas the bottom row ((g) to (i)) shows cases with no identified spindle events. FIGS. 16(a) to 16(i) show 3 sec raw signals and signals filtered in the 7-10 Hz spindle band, respectively. Online-detected slow oscillations that trigger the stimulation are indicated by thick line (1610). Intervals corresponding to light stimulation are indicated by bars (1620). The starts of intervals for the no-stimulation condition (NoSTIM-IN, NoSTIM-OUT) corresponding to in-phase and out-of-phase protocols are indicated by filled triangle (1630) and empty triangles (1640), respectively. Identified spindle generations are framed by dashed rectangles (1650).

Figure 17:
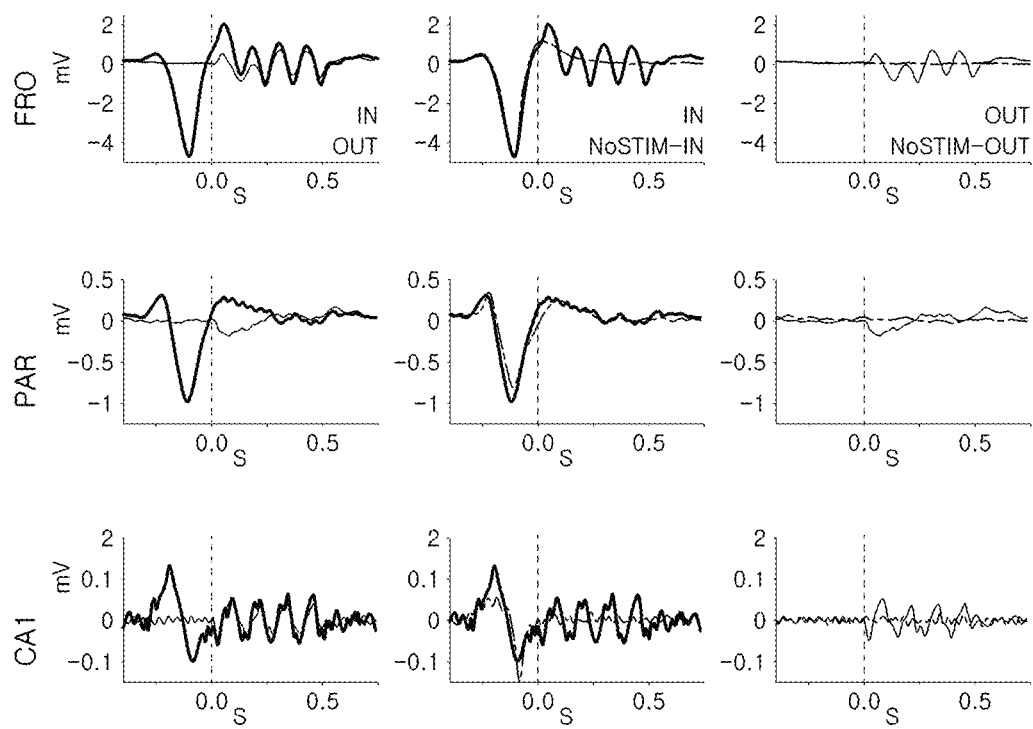
FIG. 17 shows EEGs measured at the point of time when stimulation onset starts.

FIG. 17 shows EEGs recorded in synchrony with stimulation onset. Referring to FIG. 17, it was confirmed that spindle-like activity occurred with the up-state slow oscillation during in-phase stimulation. On the contrary, the up-state slow oscillation did not emerge during out-of-phase stimulation. FIG. 17 revealed that the optogenetic spindle-like stimulation of the anterior TRN induced predominantly prefrontal cortex (FRO) spindles, which, on average, synchronized to the stimulation. Surprisingly, spindles occurred by the optogenetic stimulation was also observed in the hippocampal CA1 region. However, the spindles was not observed in parietal cortex (PAR), which indicates that the stimulated TRN regions influence the hippocampal local field potential within short delays.

Figure 18:
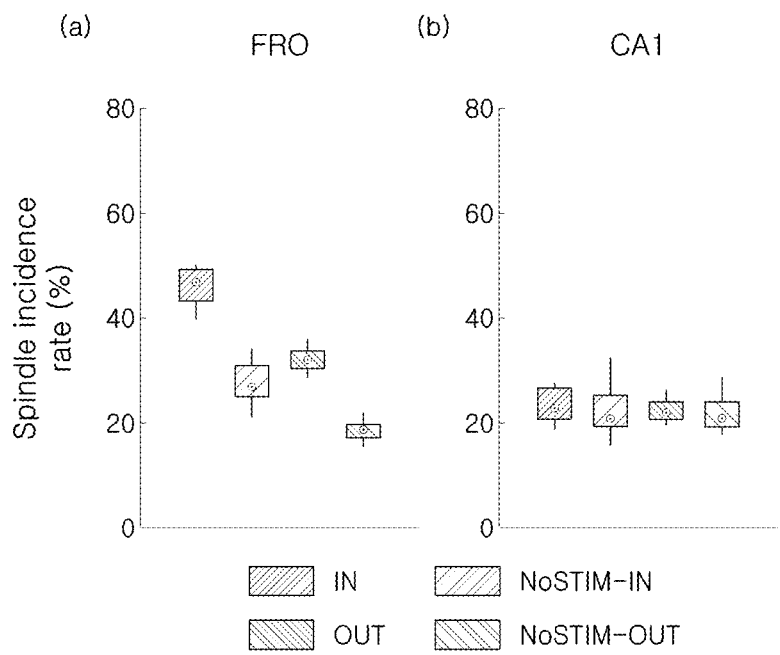

Within the time window of 750 ms after the onset of optogenetic stimulation, the spindles revealed a significantly higher spindle incidence rate for in-phase stimulation conditions than out-of-phase stimulation conditions (FIG. 18(a)). In addition, it also revealed a distinct elevation compared with the corresponding no-stimulation conditions, within the time window of 750 ms after the onset of optogenetic stimulation. In the no-stimulation condition, the spindle density for the interval corresponding to the in-phase stimulation protocol (NoSTIM-IN) was significantly higher than that for the interval corresponding to the out-of-phase stimulation protocol (NoSTIM-OUT). Further, no difference was found for the incidence of CA1 spindles following detection of stimulation or slow oscillation (FIG. 18(b)).

Figure 19:
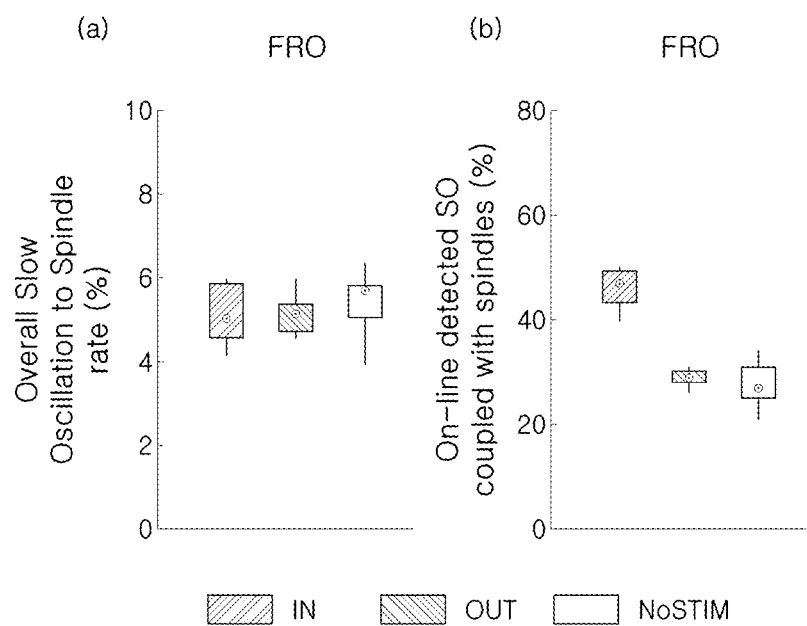
FIG. 19(a) is a graph showing the ratio of the total number of spindles to that of slow oscillations during the entire sleep period for in-phase, out-of-phase, and no-stimulation groups.
FIG. 19(b) is a graph showing slow-oscillation-spindle coupling.

Importantly, the ratio of the total spindle count to the total slow oscillation count during the total sleep time was comparable in all three conditions (FIG. 19(a)), and as a result, slow oscillation-spindle coupling (i.e., the proportion of slow oscillations that are coupled with a spindle occurred within 750 ms from detection of slow oscillations) was distinctly increased for the in-phase condition compared with both out-of-phase and no-stimulation conditions (FIG. 19(b)).

Figure 20:
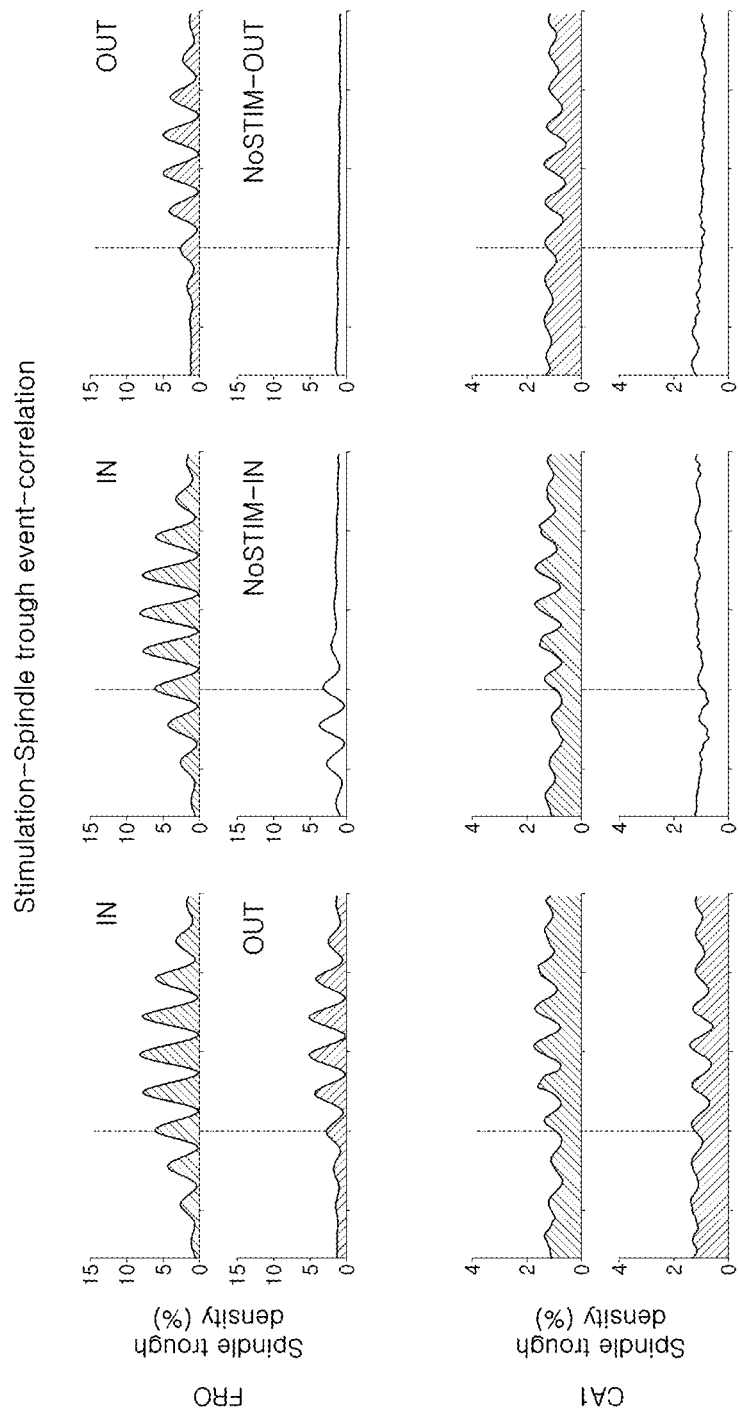
FIG. 20 is a graph showing that spindle modulation during optogenetic stimulation derives from spindle cycles of the optogenetic stimulation.

In addition, time-event correlation histograms also confirmed that spindle modulation during optogenetic stimulation, as observed not only in the cortical EEG but also in local field potential (LFP) recordings from CA1, derives from spindle cycles of optogenetic stimulation. This phenomenon was absent in the no-stimulation condition (FIG. 20). Next, the present inventors examined the influence of the TRN stimulation on inter-event intervals by determining the spindle incidence for a time window of 1.5 to 2 sec post-stimulus.). As a result, it was confirmed that the TRN stimulation have no effect on the generation of spindles during inter-event intervals.

Example 3: Confirmation of Effect of Memory Improvement of Optogenetically Induced Spindles on Hippocampal Ripples Optogenetically induced spindles preserve natural hippocampal overlap and enhance memory via triple coupling of slow oscillation, spindles, and ripples.

Figure 21:
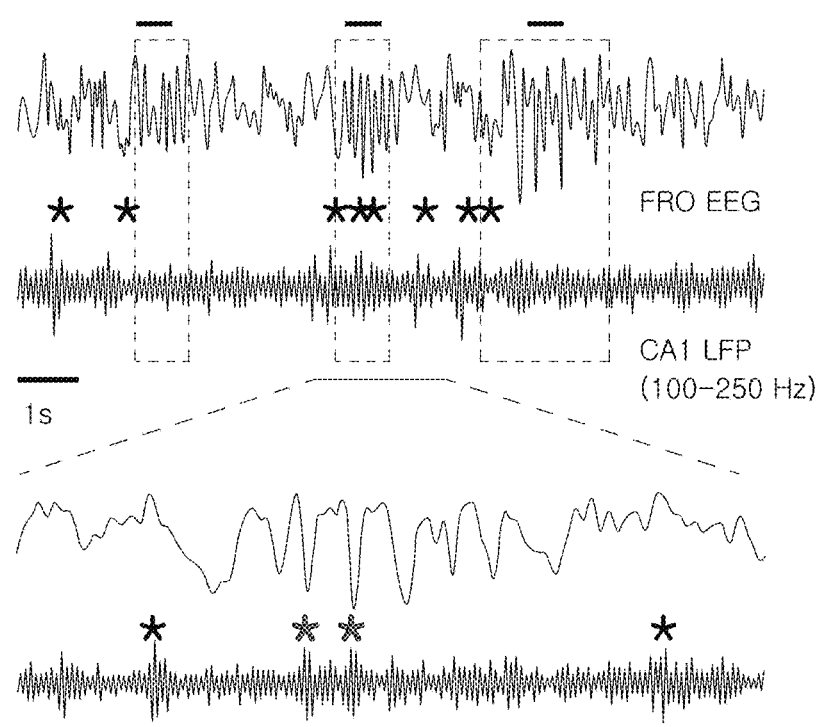
FIG. 21 is a view showing that ripple activity occurs strongly at the troughs of the spindle cycle occurring during optogenetic stimulation or the corresponding periods for no-stimulation controls.

Next, the present inventors made an attempt to examine whether spindles induced optogenetically are similar to spontaneous spindles in terms of their influence on hippocampal ripple oscillations by using protocols according to the present invention. Previous studies on human and reddens have shown a high propensity for sleep spindles to synchronize hippocampal ripples into their troughs. As a result of time-frequency analysis at the troughs of the spindle occurring during optogenetic stimulation or a corresponding no-stimulation period, a strong overlap of ripple activity into the troughs of the spindle cycle was observed (FIG. 21).

Figure 22:
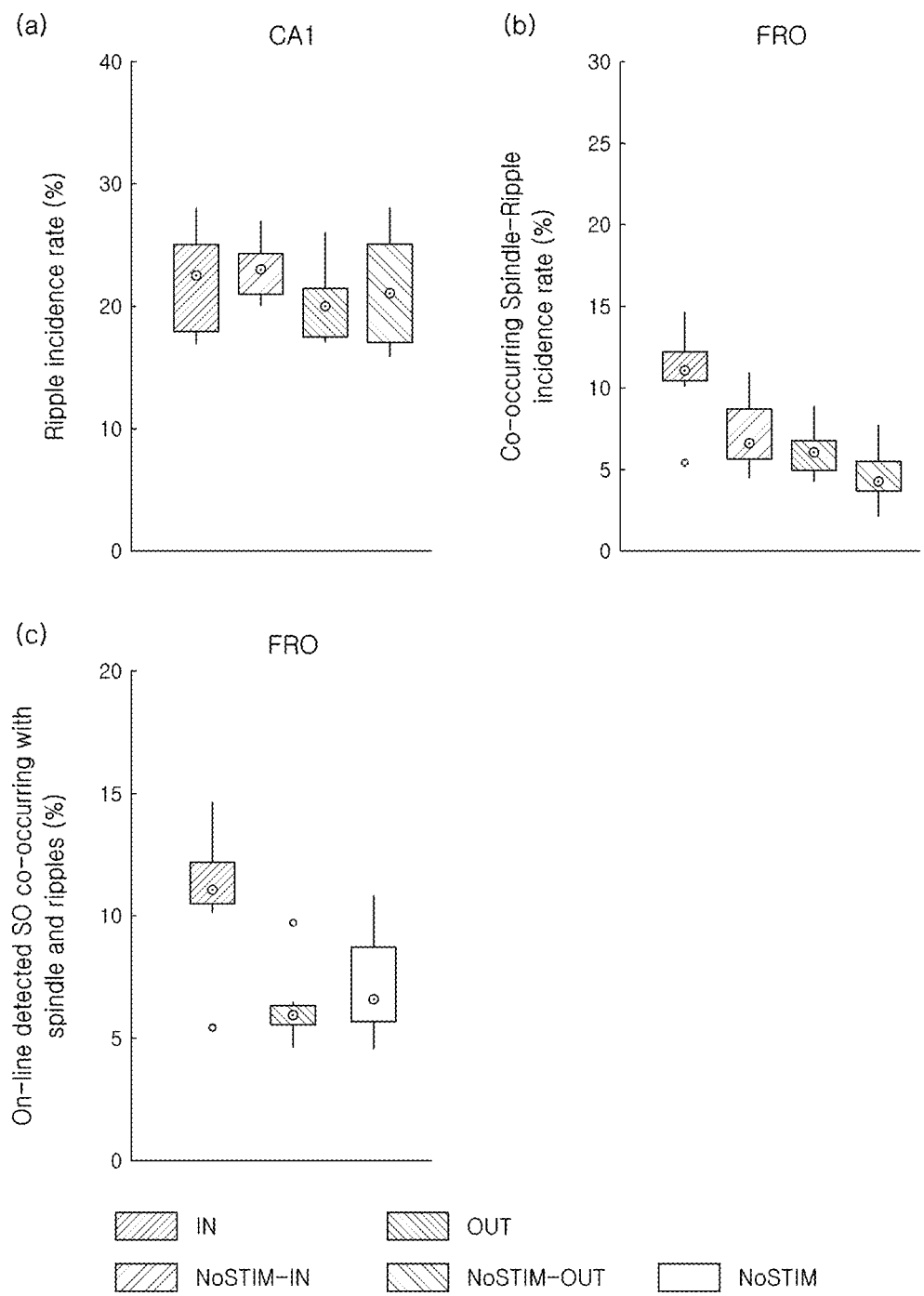
FIGS. 22(a) to 22(c) show ripple incidence rate (FIG. 22(a)), the proportion of ripples co-occurring with spindles (FIG. 22(b)), and the proportion of slow oscillation coincided with spindles co-occurring with a ripple (FIG. 22(c)), respectively.

The present inventors found that optogenetic stimulation did not affect the ripple incidence rate under any condition (FIG. 22 (a)). However, an analysis of the temporal overlap of spindle and ripple events revealed that the proportion of hippocampal ripples overlapped with spindle events during optogenetic stimulation was increased in the in-phase stimulation condition compared with the no-stimulation condition (FIG. 22 (b)). The proportion of slow oscillations overlapped with a spindle (within 750 ms after detection of slow oscillations) that overlapped with at least one ripple was significantly increased in the in-phase group compared to the no-stimulation and out-of-phase groups (FIG. 22(c)). As can be seen from slow-oscillation-spindle coupling, the degree of triple coupling of slow oscillation, spindles, and ripples has a positive correlation with the intensity of contextual memory retrieved from in-phase mice.

Figure 23:
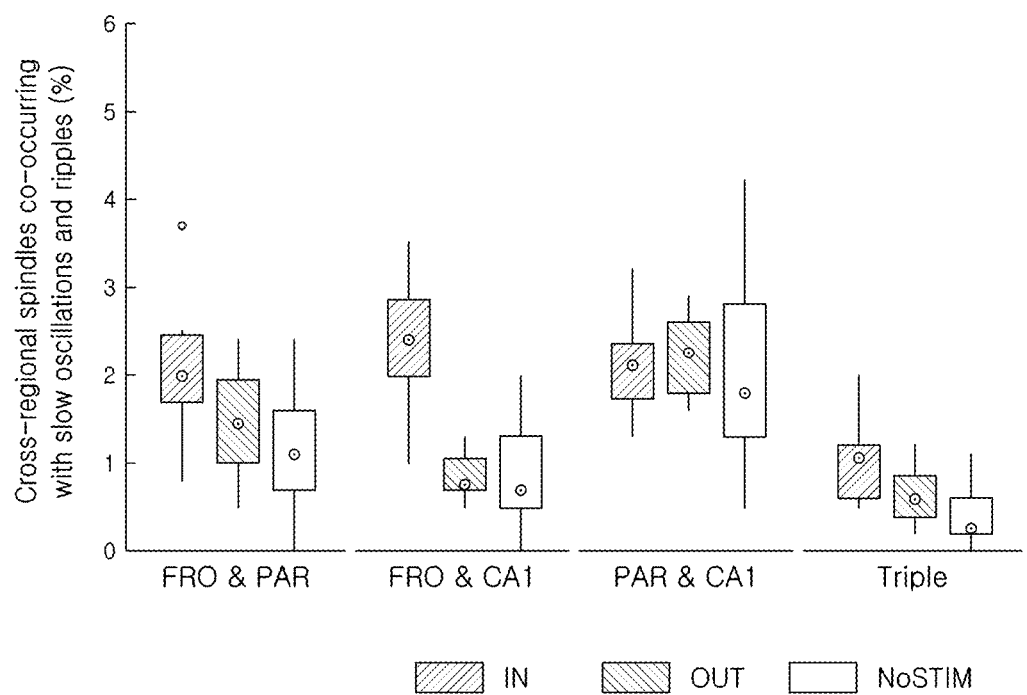
FIG. 23 is a view showing FRO-PAR, FRO-CA1, PAR-CA1, and FRO-PAR-CA1 cross-regional spindles co-occurring with slow oscillations and ripples.

Since sleep spindles are known to be spatially distributed oscillations, the present inventors further examined the cross regional occurrence of spindles during stimulation. In-phase stimulation was accompanied by a significant increase in the rate of co-occurring spindle events between FRO and PAR recordings, between FRO and CA1 recordings, and between all three recording sites (FRO-PAR-CA1) compared to the out-of-phase and no-stimulation conditions. The present inventors further examined whether these coherent spindle events also included a hippocampal ripple. As shown in FIG. 23, FRO-PAR, FRO-CA1, and FRO-PAR-CA1 cross regional spindles co-occurring with slow oscillations and ripples significantly increased for in-phase stimulation conditions compared to the out-of-phase and no-stimulation conditions.

In brief, these results indicate that in-phase stimulation produces a unique temporal-spatial pattern of the three oscillatory phenomena of interest, characterized by an increased triple coupling of slow oscillation, spindle, and ripple events. In other words, the in-phase stimulation increased the overlap of slow oscillation, spindle, and ripple events. In addition, the in-phase stimulation increased the co-occurrence of spindle events between FRO and PAR recordings, between FRO and CA1 recordings, and between all three recording sites (FRO-PAR-CA1).

Example 4: Measurement of EEGs Using Ultrasonic Stimulation Device

Figure 24:
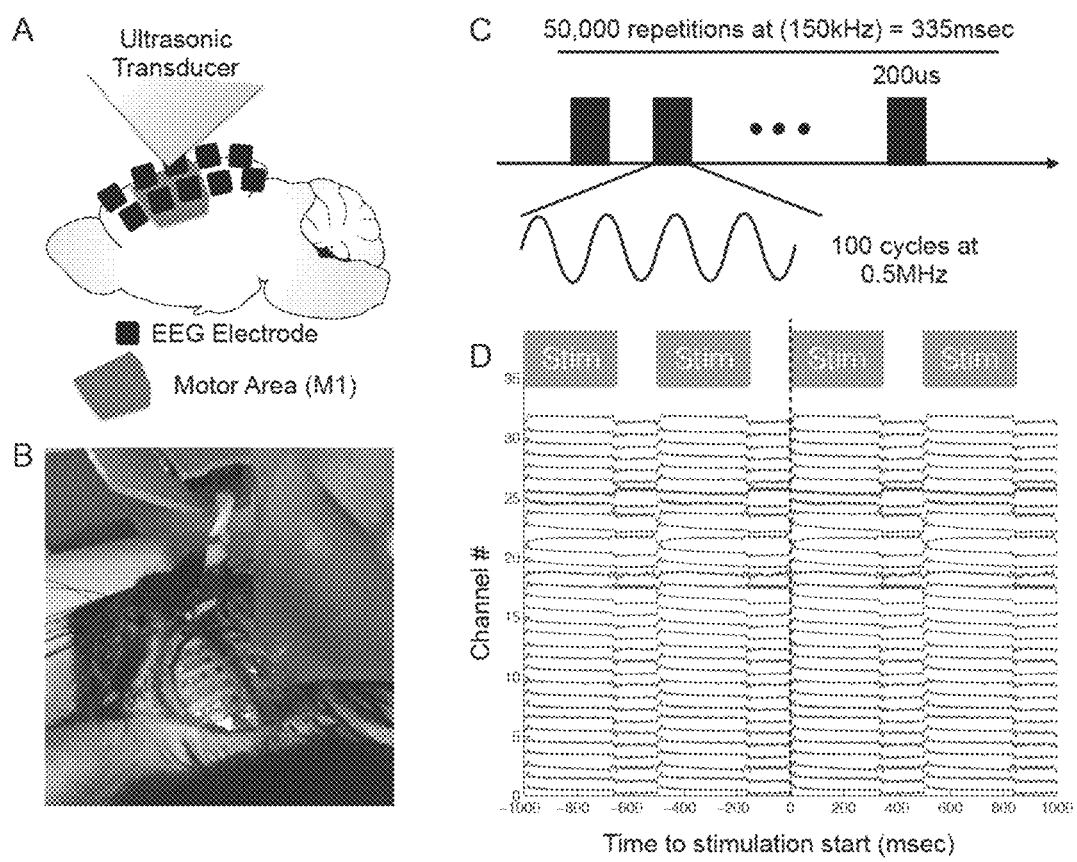
FIG. 24 is a view showing a method of applying spindle-like stimulation with ultrasonic waves, wherein FIG. 24(A) schematically shows electrodes for ultrasonic stimulation and EEG measurement.

As shown in FIG. 24, a focused ultrasound device having 32 channels was attached to a mouse's scalp, and a spindle-like stimulation was applied to a mouse brain in the same manner as in FIG. 24(C). As a result, it could be confirmed that when ultrasonic stimulation is applied to the mouse brain, changes in EEGs was observed as shown in FIG. 24(D).

The examples and the drawings annexed to the specification are merely presented to make clear a part of the technical spirit included in the above description. It will be obvious that modifications and specific embodiments that can be easily derived by those skilled in the art within the technical scope included in the specification and the drawings fall within the technical spirit and scope of the present invention.

INDUSTRIAL APPLICABILITY

The brain-stimulating device according to the present invention has an advantage in that it can reinforce a memory or reduce degradation of the memory due to dementia. In addition, the brain-stimulating device according to the present invention has an advantage in that it can reinforce hippocampus-dependent memory. Besides, the portable device according to the present invention has an advantage in that it can control and monitor the brain-stimulating device. Further, the method of assessing the performance of the brain-stimulating device according to the present invention has an advantage in that it can assess the performance of the brain-stimulating device.

The invention claimed is:

1. A method for enhancing memory, the method comprising:
   (a) measuring an EEG signal of a brain; and
   (b) applying a spindle-like stimulation to the brain in response to a generation of a slow oscillation included in the EEG signal,
   wherein the spindle-like stimulation comprises a spindle component and a slow oscillation component,
   wherein the spindle component has an envelope of the slow oscillation component,
   wherein the frequency of the spindle component of the spindle-like stimulation is within a frequency range from 11 to 16 Hz, and the frequency of the slow oscillation component of the spindle-like stimulation is less than 1 Hz, and
   wherein the slow oscillation component of the spindle-like stimulation is substantially in-phase with the slow oscillation of the EEG signal.

2. The method of claim 1, wherein the applying the spindle-like stimulation to the brain is performed by a focused ultrasound element.

3. The method of claim 1, wherein the applying the spindle-like stimulation to the brain comprises:
   (i) receiving an input of the EEG signal, and filtering a signal corresponding to a frequency band of the slow oscillation;
   (ii) detecting the generation of the slow oscillation from an output of the filtered signal, and outputting a slow oscillation detection signal;
   (iii) outputting an up-state signal corresponding to the up-state of the slow oscillation in response to the slow oscillation detection signal;
   (iv) generating a stimulation control signal during the output of the up-state signal; and
   (v) applying the spindle-like stimulation to the brain in response to the stimulation control signal.

* * * * *